(12) United States Patent
Wu

(10) Patent No.: US 8,704,827 B2
(45) Date of Patent: Apr. 22, 2014

(54) CUMULATIVE BUFFERING FOR SURFACE IMAGING

(75) Inventor: Min Wu, Fort Lauderdale, FL (US)

(73) Assignee: Mako Surgical Corp., Fort Lauderdale, FL (US)

( * ) Notice: Subject to any disclaimer, the term of this patent is extended or adjusted under 35 U.S.C. 154(b) by 1287 days.

(21) Appl. No.: 11/963,562

(22) Filed: Dec. 21, 2007

(65) Prior Publication Data

US 2009/0160855 A1 Jun. 25, 2009

(51) Int. Cl.
*G06T 17/00* (2006.01)
(52) U.S. Cl.
USPC ........... 345/420; 345/424; 345/581; 345/619; 345/630; 345/646
(58) Field of Classification Search
USPC ......... 700/184; 345/539; 705/26.62; 600/407
See application file for complete search history.

(56) References Cited

U.S. PATENT DOCUMENTS

| | | | | |
|---|---|---|---|---|
| 5,122,966 | A |  | 6/1992 | Jansen et al. ............... 364/474.2 |
| 5,710,709 | A | * | 1/1998 | Oliver et al. .................. 700/184 |
| 6,157,374 | A | * | 12/2000 | West et al. ..................... 345/539 |
| 2003/0025692 | A1 | * | 2/2003 | Lu et al. ........................ 345/418 |
| 2004/0015070 | A1 |  | 1/2004 | Liang et al. ................... 600/407 |
| 2004/0186612 | A1 | * | 9/2004 | Edwards et al. .............. 700/160 |
| 2005/0038642 | A1 | * | 2/2005 | Rameau et al. ................... 704/1 |
| 2006/0094951 | A1 | * | 5/2006 | Dean et al. .................... 600/407 |
| 2006/0142657 | A1 |  | 6/2006 | Quaid et al. .................. 600/424 |
| 2007/0198367 | A1 | * | 8/2007 | Yamagata et al. ......... 705/26.62 |

FOREIGN PATENT DOCUMENTS

WO WO 02/061688 A2 8/2002
WO WO 2007/000144 1/2007 ............. G06T 11/00

OTHER PUBLICATIONS

International Search Report and Written Opinion for International Application No. PCT/US2007/088702, Mailed Aug. 14, 2009 (13 pages).
O'Driscoll, Shawn W. et al. "*Arthroscopy.*" *Reconstructive Surgery of the Joints*. Ed. Bernard F. Morrey, M.D. New York: Churchill Livingstone, 1996. 587-608.
Goldfeather, Jack et al. "Near Real-Time CSG Rendering Using Tree Normalization and Geometric Pruning." *IEEE Computer Graphics & Applications* May 1989: 20-28.
Hable, John et al. "Blister: GPU-based Rendering of Boolean Combinations of Free-form Triangulated Shapes." Association for Computer Machinery, Inc, 2005. 1024-1031.
Hable, John et al. "CST: Constructive Solid Trimming for Rendering BReps and CSG." *IEEE Transactions on Visualization and Computer Graphics* Sep./Oct. 2007:1004-1014.
Stewart, Nigel et al. "An Improved Z-Buffer CSG Rendering Algorithm." Workshop on Graphics Hardware, 1998. 25-30.

* cited by examiner

*Primary Examiner* — Phi Hoang
(74) *Attorney, Agent, or Firm* — Foley & Lardner LLP

(57) ABSTRACT

The description relates to surgical computer systems, including computer program products, and methods for cumulative buffering for surface imaging. A display image is buffered that has been saved from a previous update. A model representing a tool is subtracted from the buffered display image. The subtracted display image is displayed using a CSG technique at a fixed angle. The subtracted display image is saved. This process is repeated so that the displayed image is cumulatively changed with each change in location of the model representing the tool.

19 Claims, 17 Drawing Sheets

CUMULATIVE BUFFERING FOR SURFACE IMAGING

BACKGROUND OF THE INVENTION

1. Field of the Invention

The invention relates to surgical computer systems, including computer program products, and methods for cumulative buffering for surface imaging.

2. Description of Related Art

The use of computers and computerized equipment is becoming more prevalent during surgical procedures. If the position of the surgical instrument is tracked by a surgical computer system, a computer can generate a visualization of the surgical instrument's position relative to the patient's anatomy. A visualization is, for example, a simulated three-dimensional image displayed on a computer screen. The visualization can be based on images of the patient's actual anatomy (such as CT scans). If the surgical instrument is removing tissue from the anatomy, e.g., a burr removing bone tissue in preparation to receive an implant, the visualization can be a simulated image of the anatomy showing the removed tissue based on the position of the instrument. Such an exemplary surgical computer system is described in detail, for example, in U.S. Patent Publication 2006/0142657, published Jun. 29, 2006, which is hereby incorporated by reference herein in its entirety.

The exemplary surgical computer system can use, for example, the "isovol" technique, or iso-volume technique. Using this technique, the volume of the bone area being worked on and the volume of the burr being used are calculated. The volume of the burr is then subtracted from the volume of the bone. This subtraction is performed by a CPU of a computer. From this subtraction process, a surface model of the bone area is calculated, again using the CPU. A graphics card generates the visualization based on the surface model and it is displayed on the screen. When the burr is moved to a new location, the burr volume is subtracted from the bone area at the burr's new position. A new surface model is then calculated. Because the old surface model is no longer accurate, it is cleared from the buffer and the new surface model is buffered. This is sometimes referred to as the "clear and display" approach. This process is continuously repeated as the burr is moved. Because this processing is done in real time, as the burr is moving, the resolution is low to allow for the necessary computations.

Another technique that is used for three-dimensional modeling is constructive solid geometry (CSG). CSG is typically used in geometric modeling, such as a Computer Aided Design (CAD) package for modeling components. In CSG techniques, complex shapes are built from simple shapes by volumetric Boolean operations, i.e. union, intersection, and subtraction. A complex shape is specified by a CSG expression, which is commonly stored as a CSG tree whose leaf nodes represent basic shapes (primitives such as sphere, cylinder, and box) and inner nodes denote Boolean operations. See, e.g., the examples shown at the constructive solid geometry web page at wikipedia, the online encyclopedia.

Image-based CSG algorithms are a category of algorithms for z-buffer graphics hardware that generate "just an image" of a CSG shape without calculating a description of the final object geometry. Image-based CSG takes advantage of the hardware acceleration in a video card (also referred to as a graphics card), which can improve rendering speed. CSG also can produce less visual artifacts than a possibly approximated 3D geometry.

The CSG techniques have better resolution than the isovol technique and CSG can allocate its visualization tasks to a video card, and thus increase CPU performance and resolution. However, as the burr is moved, the number of leaf nodes (primitives) on CSG tree grows larger and larger, and this makes the conventional "clear and display" approach algorithm described above not feasible for sophisticated tasks such as visualizing a bone preparation process.

SUMMARY OF THE INVENTION

In one aspect, there is a method of cumulative buffering for surface imaging. The method includes buffering a display image saved from a previous update and subtracting a model representing a tool from the buffered display image. The method also includes displaying the subtracted display image at a fixed angle and saving the subtracted display image.

In another aspect, there is a surgical computer system that includes at least one video card. The video card is configured to buffer a display image saved from a previous update and subtract a model representing a tool from the buffered display image using a CSG technique. The video card is also configured to display the subtracted display image at a fixed angle and save the subtracted display image.

In other examples, any of the aspects above can include one or more of the following features. The model representing the tool can be displayed using the CSG technique, a different CSG technique, or both, at the fixed angle. The steps of buffering, subtracting, displaying, and saving can be repeated in response to a received update of location of the tool.

Subtracting can include representing a workpiece model using a plurality of layer models. Depths of back surfaces of the model representing the tool are determined. A surface area is determined at a location of the model representing the tool where each pixel on the surface has depth less than the depths of the back surfaces of the model representing the tool. Displaying can include displaying the subtracted surface in the identified area in a corresponding color of a first layer model. The first layer model can have a depth greater than a second layer model from the plurality of layer models at the location of the model representing the tool. The first layer model can have a depth less than a second layer model from the plurality of layer models at the location of the model representing the tool. Each pixel on the surface area can be determined that has depth falling within a range of a depth of a front surface of the first layer model and a depth of a back surface of the first layer model, inclusive.

Subtracting can include representing a workpiece model using a plurality of layer models, where the plurality includes a top most layer model, a bottom most layer model, and one or more intermediate layer models. Depths of front surfaces of the top most layer model can be determined. A surface area of the workpiece model can be identified where each pixel on the surface area has depth greater than the depths of front surfaces of the top most layer model and the identified surface area can be displayed in a corresponding color of the top most layer model.

Subtracting can include, for each of the one or more intermediate layer models, determining depths of front surfaces of a particular intermediate layer model. A surface area of the workpiece model can be identified where each pixel on the surface area has depth greater than the depths of front surfaces of the particular intermediate layer model and the identified surface area can be displayed in a corresponding color of the particular intermediate layer model.

Subtracting can include determining depths of front surfaces of the bottom most layer model. A surface area of the workpiece model can be identified where each pixel on the surface area has depth greater than the depths of front surfaces of the bottom most layer model and the identified surface area can be displayed in a corresponding color of the bottom most layer model.

Subtracting can include determining depths of back surfaces of the model representing the tool. A surface area of a workpiece model can be identified at a location of the model representing the tool where each pixel on the surface area has depth less than the depths of the back surfaces of the model representing the tool. The identified surface area can be displayed in a corresponding color of a wall layer model if the location of the model representing the tool is outside a boundary of the wall layer model. The identified surface area can be displayed in a color corresponding to an appropriate layer model based on depth if the location of the model representing the tool is within the boundary of the wall layer model.

The display image can be a first display image and the fixed angle can be a first fixed angle. In such examples, a second display image saved from a previous update can be buffered, where the second display image has a viewing angle at a second fixed angle different than the first fixed angle. The model representing the tool from the buffered second display image is subtracted using the CSG technique. The subtracted second display image is displayed at the second fixed angle and the subtracted second display image is saved.

An implant can be represented within the display image. An implant can be represented within the display image using a first layer model from a plurality of layer models. Buffering can include copying the display image saved from the previous update. The display image can be based on a medical image associated with a patient. The model representing the tool can include a burr model. The burr model can include a spherical primitive. The subtracted display image can be displayed at a high resolution.

In another aspect, there is computer program product, tangibly embodied in an information carrier. The computer program product includes instructions being operable to cause a data processing apparatus to perform any of the techniques above.

Any of the aspects or features described herein may include one or more of the following advantages. The use of a cumulative buffer enables faster processing of an image. The use of CSG allows a visualization of higher resolution. The techniques can be used with any number of layer models. The use of processing the image enables much of the visualization processing to be performed on a video card, freeing up CPU resources for other tasks. A display can be generated showing multiple viewing angles so that no particular viewing angle needs to be readjusted.

BRIEF DESCRIPTION OF THE DRAWINGS

The accompanying drawings, which are incorporated in and constitute a part of this specification, illustrate embodiments of the invention and together with the description serve to explain principles of the invention.

DETAILED DESCRIPTION OF PREFERRED EMBODIMENTS

To generate a high resolution visualization of a bone (or workpiece) preparation, the techniques described herein modify a display frame buffer in a "cumulative" fashion rather than "clear and display" fashion between rendering steps for each display cycle. The cumulative buffering scheme saves the steps of clearing and displaying updated image frames by continually incrementing changes onto the previously displayed image frames. The cumulative buffering of display frames is inherently not compatible with the isovol technique, but is compatible with a CSG technique which utilizes a video card for the cumulative buffering task. This cumulative buffering algorithm makes CSG technique practically applicable to visualize bone preparation with currently available video cards.

Figure 1:
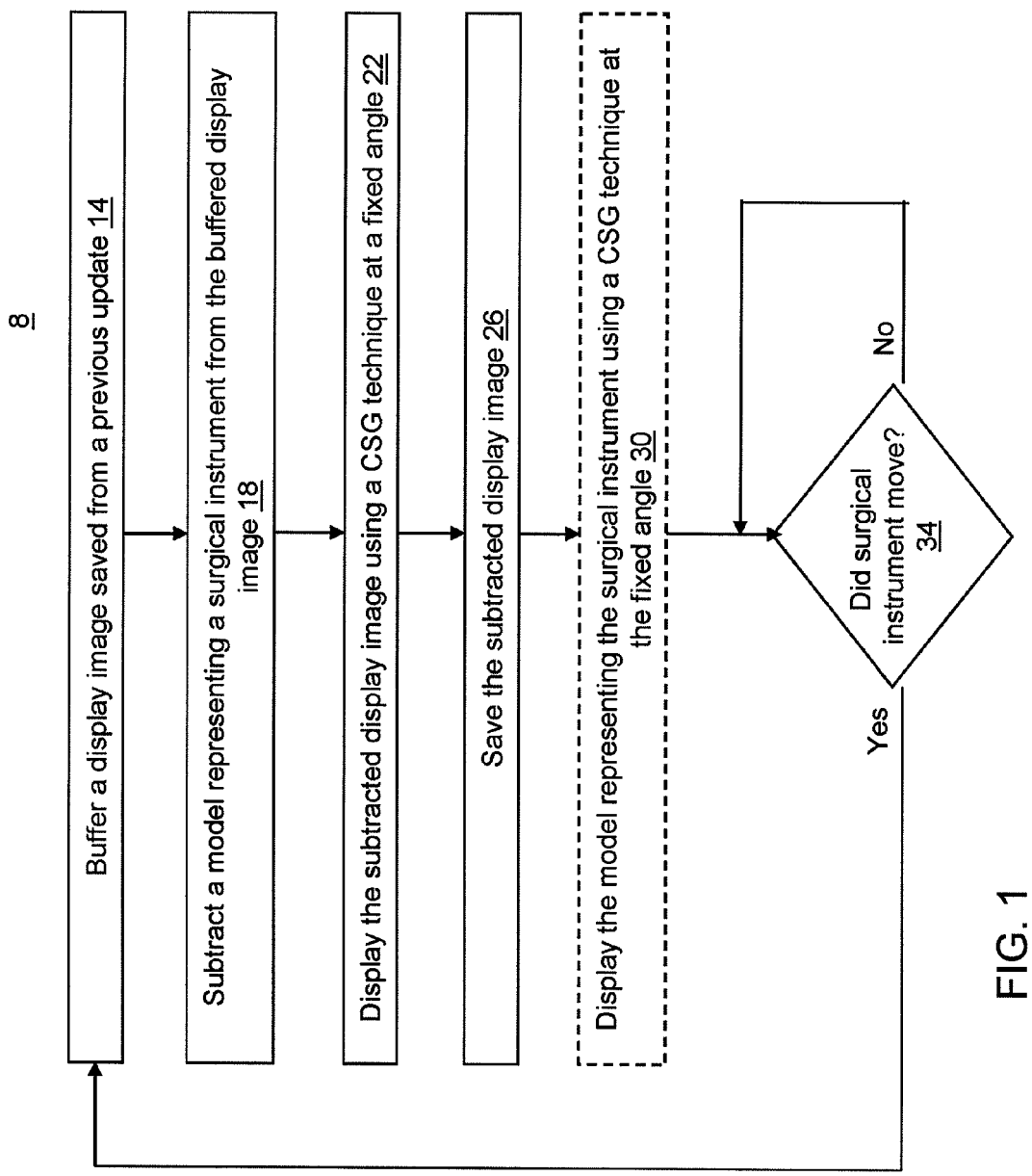
FIG. 1 illustrates an exemplary process of cumulative buffering for surface imaging.

FIG. 1 illustrates an exemplary process 8 for cumulative buffering for surface imaging. The process 8 can be performed by a video card that is included in a surgical computer system. The video card can have, for example, a graphics processing unit (GPU) that performs these processes. The video card first generates an initial image of a particular surface at a particular viewing angle. The particular viewing angle remains fixed during the cumulative buffering process. The particular surface can be, for example, a surface of a workpiece, such as a bone surface from which a surgeon is removing tissue with a surgical instrument or tool. The video card buffers a display image saved from a previous update (14). During the first pass of the process 8, the buffered display image will be the initial image because there isn't a previous update yet. All subsequent passes through the process 8 will result in having a previous update that is buffered.

The video card subtracts a model representing a surgical instrument or tool from the buffered display image (18). This process of subtracting is described in more detail below. The video card displays the subtracted display image using a CSG technique at a fixed angle (22). For example, in one CSG technique, where a CSG tree is used, the bone model and the surgical instrument are treated as primitives. They are added as leaf nodes with an inner node of subtraction as appropriate to represent the removal of bone tissue from the volume that was taken up by the surgical instrument. For example, as described below, if the surgical instrument is a spherical burr, then the representative primitive is a sphere with the same diameter as the burr, and the primitive representing that burr is added to the CSG tree with a subtraction operator based on the location of the burr relative to the bone model.

With the subtraction performed, the video card saves the subtracted display image (26). The step can include, for example, updating the buffered display frame on which the subtraction was performed. This saved image now becomes the previous update when the process 8 is repeated (i.e., the previous update in step (14) refers to the saved update in step (26)). In this sense, the process 8 is a cumulative buffering in that the subtraction process is performed on the prior display. The video card can optionally display the model representing the surgical instrument using a CSG technique at the fixed angle (30).

The tracking system determines whether the surgical instrument moved (34). This can be done, for example, by receiving input from the CPU of the surgical computer system indicating that the surgical instrument is at a new location (e.g., as described below with respect to FIG. 17). In some examples, the sampling rate for the position of the surgical instrument can be 10 Hz. If the surgical instrument moved, then the process 8 is repeated for the new position. The video card buffers the display image saved from a previous update (14). As mentioned above, this is the image saved at the previous step (26). The video card subtracts the model representing the surgical instrument at its new position from the buffered display image (18). The new subtracted display image is displayed (22) and saved (26).

Figure 2:
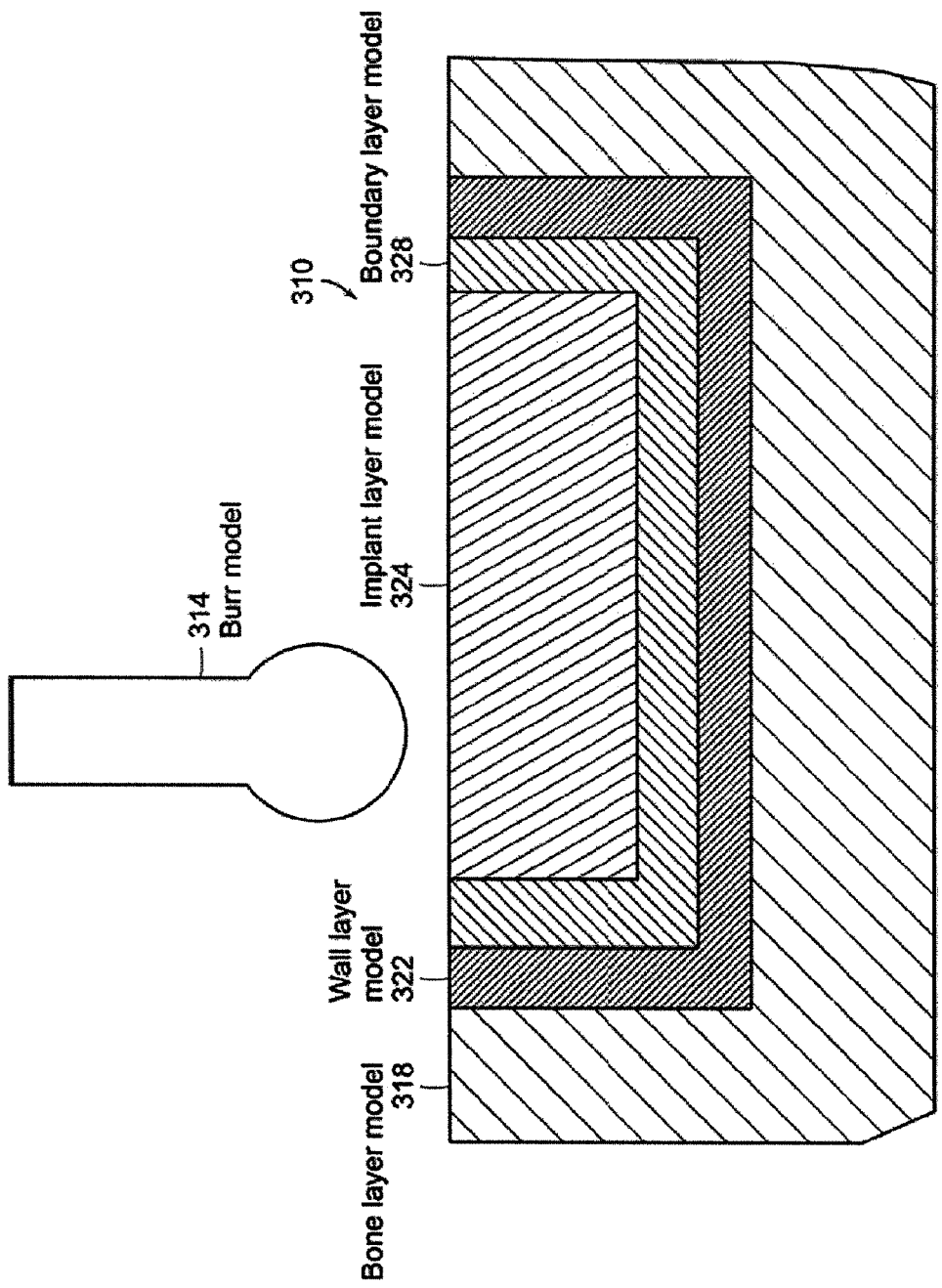
FIG. 2 illustrates a front cross section view of an exemplary bone preparation model and a burr model.

FIGS. 2-11 illustrate the subtraction process in more detail. FIG. 2 illustrates a front view of an exemplary bone preparation model 310 and a burr model 314. The bone preparation model 310 includes four layer models, which are a bone layer model 318, a wall layer model 322, an implant layer model 324, and a boundary layer model 328. Although four layers are used in FIG. 2, the techniques described herein can work with any number of layers. For example, if multiple boundary layers are needed, the single boundary layer 328 can be divided into multiple boundary layers. The four layers can be represented by different colors. For example, the bone layer model 318 can be orange, the wall layer model 322 can be red, the implant layer model 324 can be green, and the boundary layer model 328 can be white. In the black and white figures, each color is represented by a different hashing pattern.

The bone layer model 318 represents the bone from which tissue will be removed. This can be based on an actual patient's anatomy using, for example, that patient's medical images, such as CT scans of the bone. The implant layer model 324 represents the bone tissue that must be removed so that the implant can be fitted into the bone. The boundary layer model 328 represents a spacing around the implant layer model 324 into which the burr model 314 can travel. For example, because the burr model 314 is spherical, it cannot cut sharp corners. The burr model 314 is allowed to extend some distance beyond the implant layer model 324 to ensure the entire implant layer model 324 is removed. However, the burr model 314 cannot be allowed to extend too far from the implant layer model, or excessive amounts of tissue could be removed. The wall layer model 322 represents a "hard stop" boundary that the burr model 314 cannot go past. In some surgical computer systems, such as the exemplary system 210 shown in FIG. 17, a haptic device 230 prevents a surgeon from moving the surgical instrument (represented by the burr model 314) past the boundary represented by the wall layer model 322.

Figure 3:
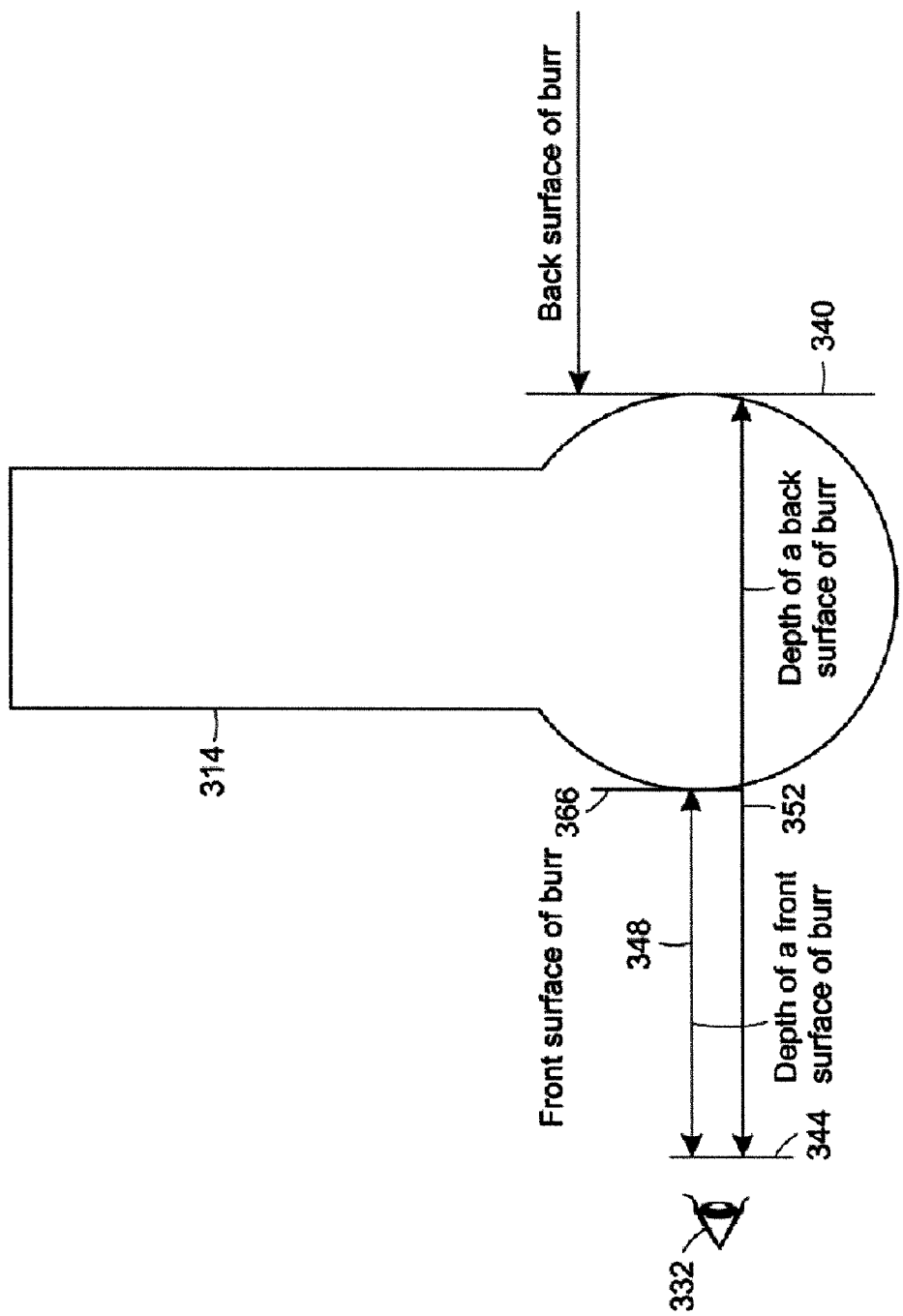
FIG. 3 illustrates surfaces and depths with respect to the burr model.

FIG. 3 illustrates the depths and surfaces of the burr model 314 from a particular viewing angle, represented by an eye 332. From the viewing angle of the eye 332, the burr model 314 has a front surface 366 and a back surface 340. The front surface 366 is the surface closest to the eye 332 and the back surface 340 is the surface farthest from the eye 332. The depth of the two surfaces can be calculated using a common point of measurement. For example, the surface 344 of the eye 332 can be used as a common point of measurement. Other common points can also be used. Using the common point of measurement 344, a processor can determine a distance 348 from the common point 344 to the front surface 366 of the burr model 314. This distance is referred to as the depth of the front surface 366 of the burr model 314. Similarly, the processor can determine a distance 352 from the common point 344 to the back surface 340 of the burr model 314. This distance is referred to as the depth of the back surface 340 of the burr model 314. In this case, the depth of the back surface 340 is greater than the depth of the front surface 366. In some cases, the algorithm uses a depth as a relative comparison to another depth, and therefore the common point used to calculate the depths can be arbitrary, as long as that point is common for the two depths being relatively compared.

Figure 4:
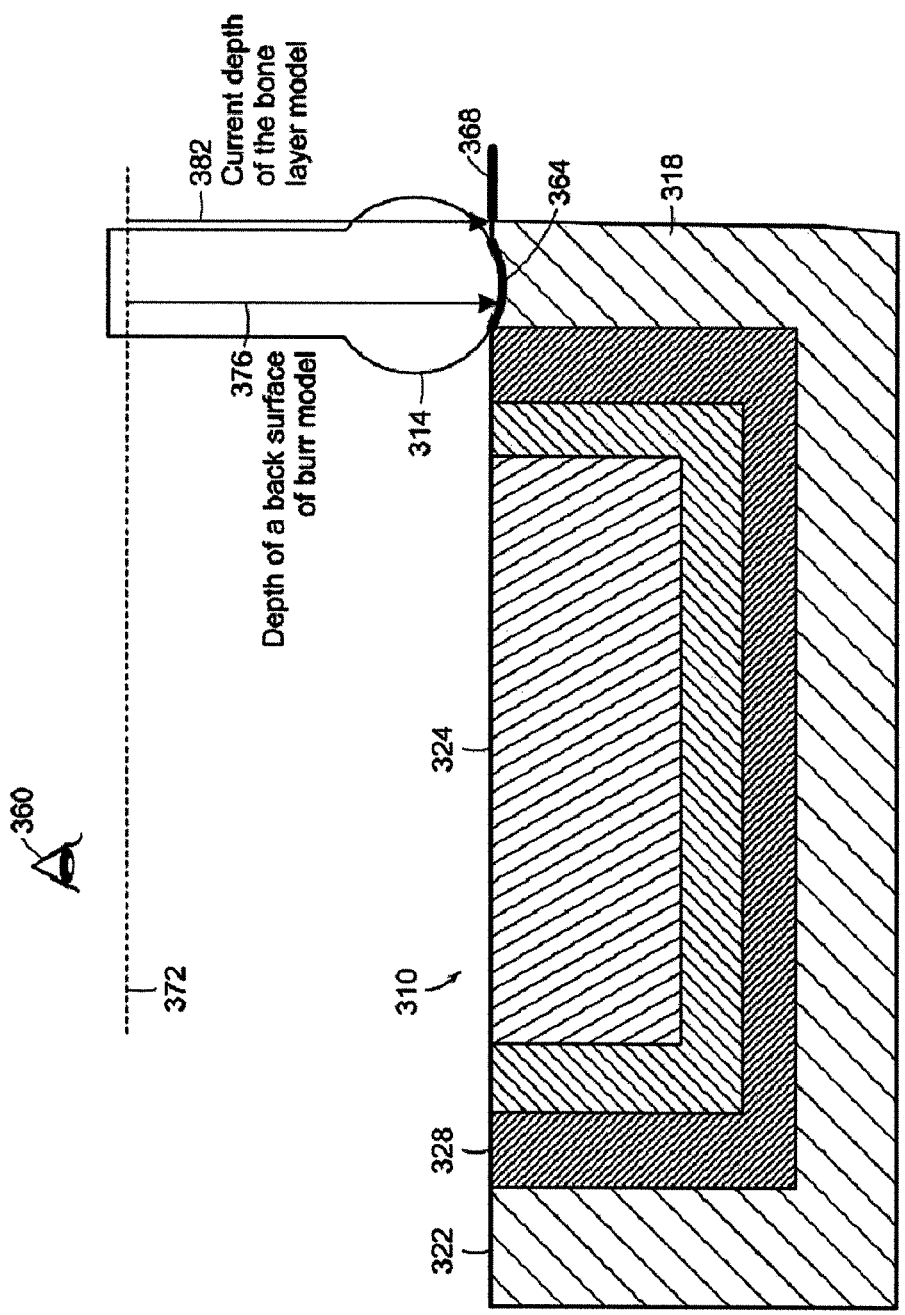
FIG. 4 illustrates a front cross section view of an exemplary bone preparation model and a burr model where the viewing angle is looking down at the top surface of the bone preparation model.

FIG. 4 illustrates the front view of the bone preparation model 310 and the burr model 314 where the particular viewing angle is looking down at the top surface of the bone preparation model 310. The viewing angle is represented by an eye 360. From the viewing angle of the eye 360, the burr model 314 has a number of back surfaces 364. The back surfaces 364 are the surfaces facing away from the eye 360. From the viewing angle of the eye 360, the bone model 310 also has a closest surface 368, which in this case will be referred to as the top surface, since the viewing angle is looking down at the top of the bone model 310. The depth of the two surfaces can be calculated using a common point of measurement. For example, the surface 372 of the eye 360 can be used as a common point of measurement. The distance 376 represents the depth of the back-most of the back surfaces 364 of the burr model 314. The distance 382 represents the depth of the top surface 368 of the bone model 310.

In the illustrated example of FIG. 4, the surgical instrument, represented by the burr model 314, has penetrated the bone, represented by bone layer model 318 and thus cutting and removal of bone tissue has occurred. The processor subtracts the current position of the burr model 314 from the bone layer model 318. For example, using a CSG technique, the burr model 314 and the bone layer model 318 can each be treated as primitives, with the resulting surface being, for example, the Boolean difference between the two. To generate the display image showing the area of penetration of the surgical instrument into the bone, the processor determines the location of the burr model 314 and the depth of back surfaces 364 of the burr model 314 at this location. The processor also identifies the surface area of the bone layer model 318 in this location where each pixel on a surface of the bone layer model 318 has depth less than the depths of the back surfaces 364 of the burr model 314.

Figure 5:
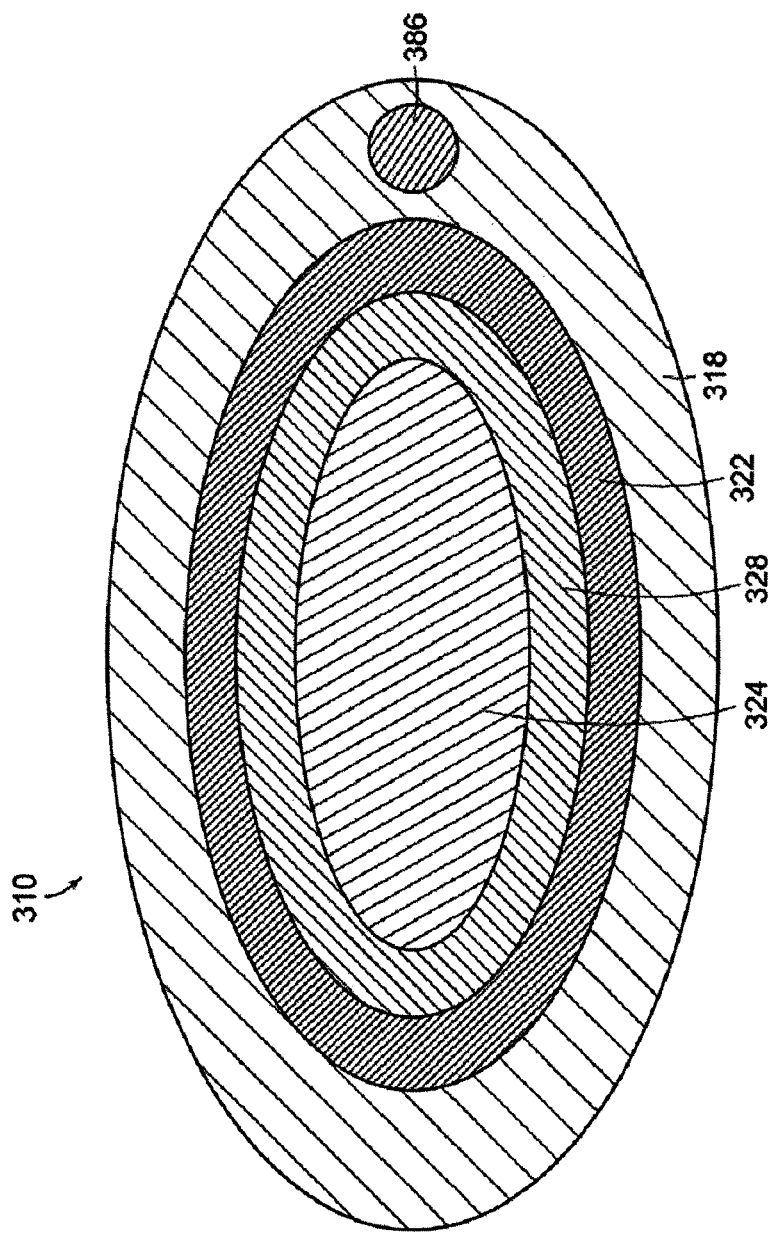
FIG. 5 illustrates a top view of the bone model corresponding to FIG. 4.

As shown in FIG. 5, which illustrates a top view of the bone model 310, this identified surface area can be shown in the display image. For example, the processor draws a surface area 386 indicating the identified surface area from the depth analysis. The processor draws the surface area 386 in a corresponding color of the bone layer model 318. In some examples, the surface area 386 is drawn in red because this location is outside of the wall layer model 322.

Figure 6:
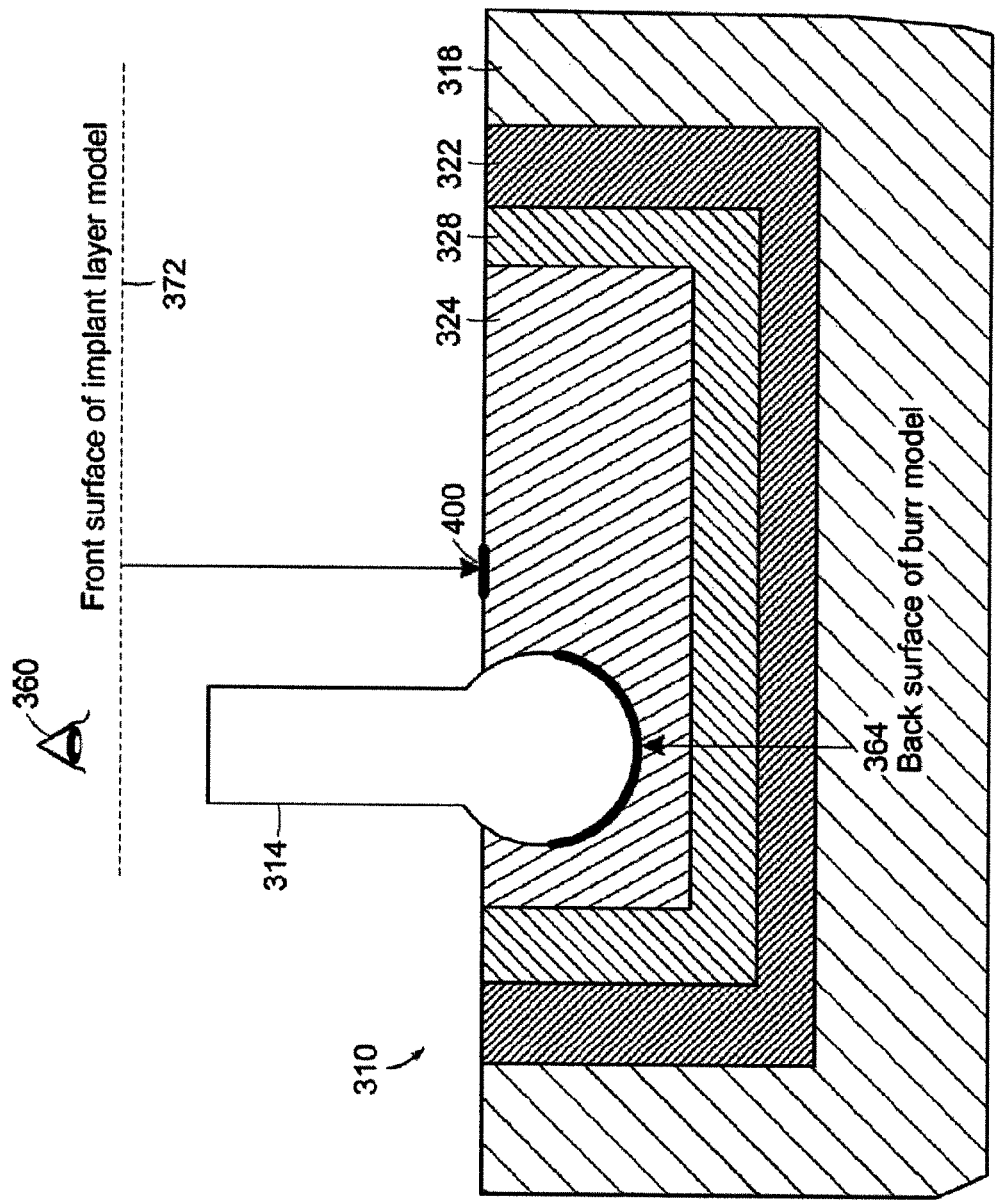
FIG. 6 illustrates the front view of the bone preparation model and the burr model using the same viewing angle illustrated in FIG. 4, with the burr model in a different position.

FIG. 6 illustrates the front view of the bone preparation model 310 and the burr model 314 using the same viewing angle illustrated in FIG. 4, represented by the eye 360. In FIG. 6, the position of the burr model 314 has changed from its position in FIG. 4 and is now within the implant layer model 324. Similar to the process described above, the processor determines the depths of front surfaces 400 (front with respect to the viewing angle, which in this case is looking at the top of the bone model 310, so may also be referred to as top surfaces) of the most top layer model, the implant layer model 324. The processor will render depths of front surfaces 400 of the implant layer model 324 in a color corresponding to the implant layer model 324, such as the color green. The processor identifies the surface area of the bone model 310 at the location of the burr model 314 where each pixel on a surface of the implant layer model 324 has depth less than the depths of the back surfaces 364 of the burr model 314. This surface area represents the area from which bone material has been removed from the bone using the burr.

Figure 7:
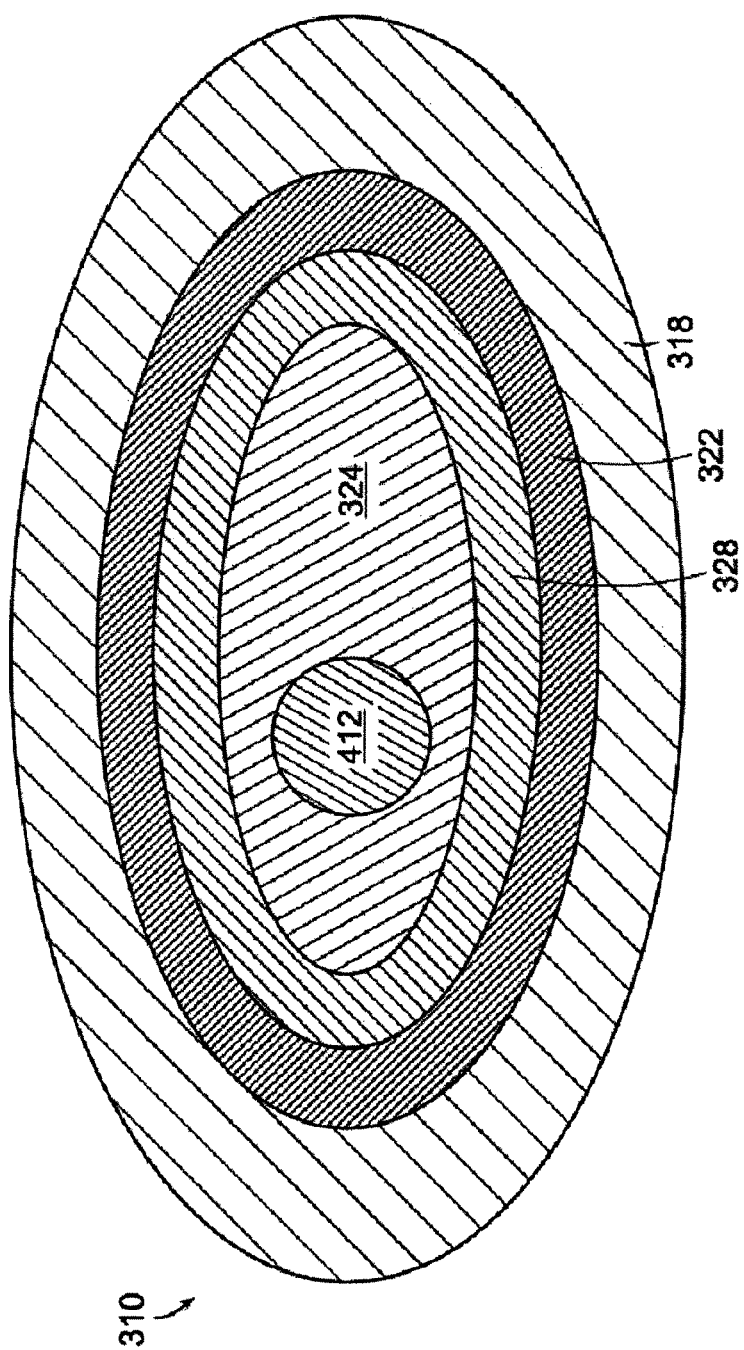
FIG. 7 illustrates a top view of the bone model corresponding to FIG. 6.

FIG. 7 illustrates a top view of the bone model 310 after the subtraction has taken place. The top view includes the identified area 412 from which the burr removed bone tissue. Because the depth of the burr model 314 remained within the implant layer model 324 (as can be seen from FIG. 6) the processor draws the identified subtracted surface area in the color green, the corresponding color of the implant layer model 324. When drawing a three-dimensional image, the depth of the surface area 412 is greater than the rest of the top surface of implant layer model 324 because material has been removed equivalent to the size of the burr, but the color remains green because the depth of the burr has not reached the next layer in the bone model 310. Or stated in relative terms, the depth of the pixels in the identified surface area 412 is less than the depth of the top surfaces of the boundary layer model 328.

Figure 8:
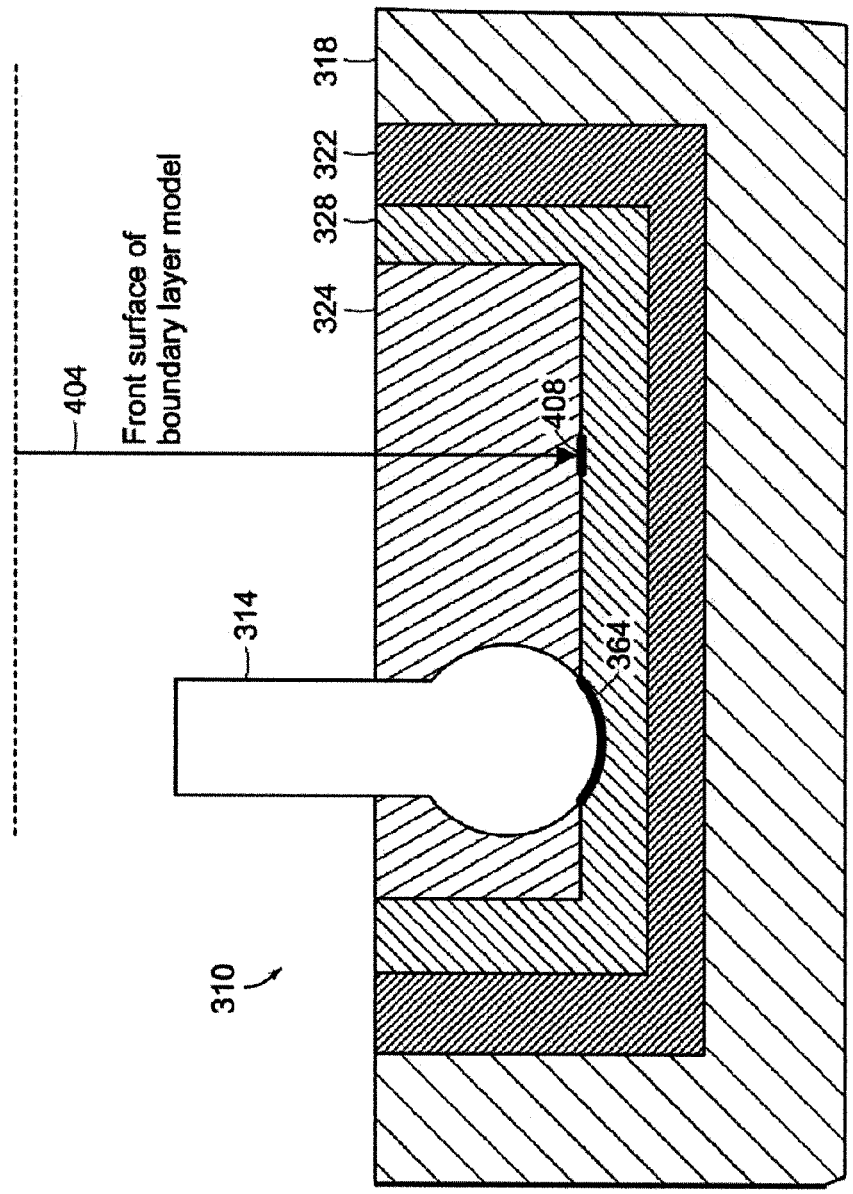
FIG. 8 illustrates the front view of the bone preparation model and the burr model using the same viewing angle illustrated in FIG. 6, with the burr model in a different position.

FIG. 8 illustrates the front view of the bone preparation model 310 and the burr model 314 using the same viewing angle illustrated in FIG. 6, represented by the eye 360. In FIG. 8, the position of the burr model 314 has changed from its position in FIG. 6 and is now deeper within the implant layer model 324 and has penetrated into the boundary layer model 328. Similar to the process described above, the processor determines the depth (indicated by arrow 404) of front surfaces 408 of the top of the boundary layer model 328. The processor will render depths of front surfaces 408 of the boundary layer model 328 in the color white, the color corresponding to the boundary layer model 328. The processor identifies the surface area of the bone model 310 at the location of the burr model 314 where each pixel on a surface of the boundary model layer 328 has depth less than the depths of the back surfaces 364 of the burr model 314. This surface area represents the area from which bone material has been removed from the bone using the burr within the boundary layer model 328.

Figure 9:
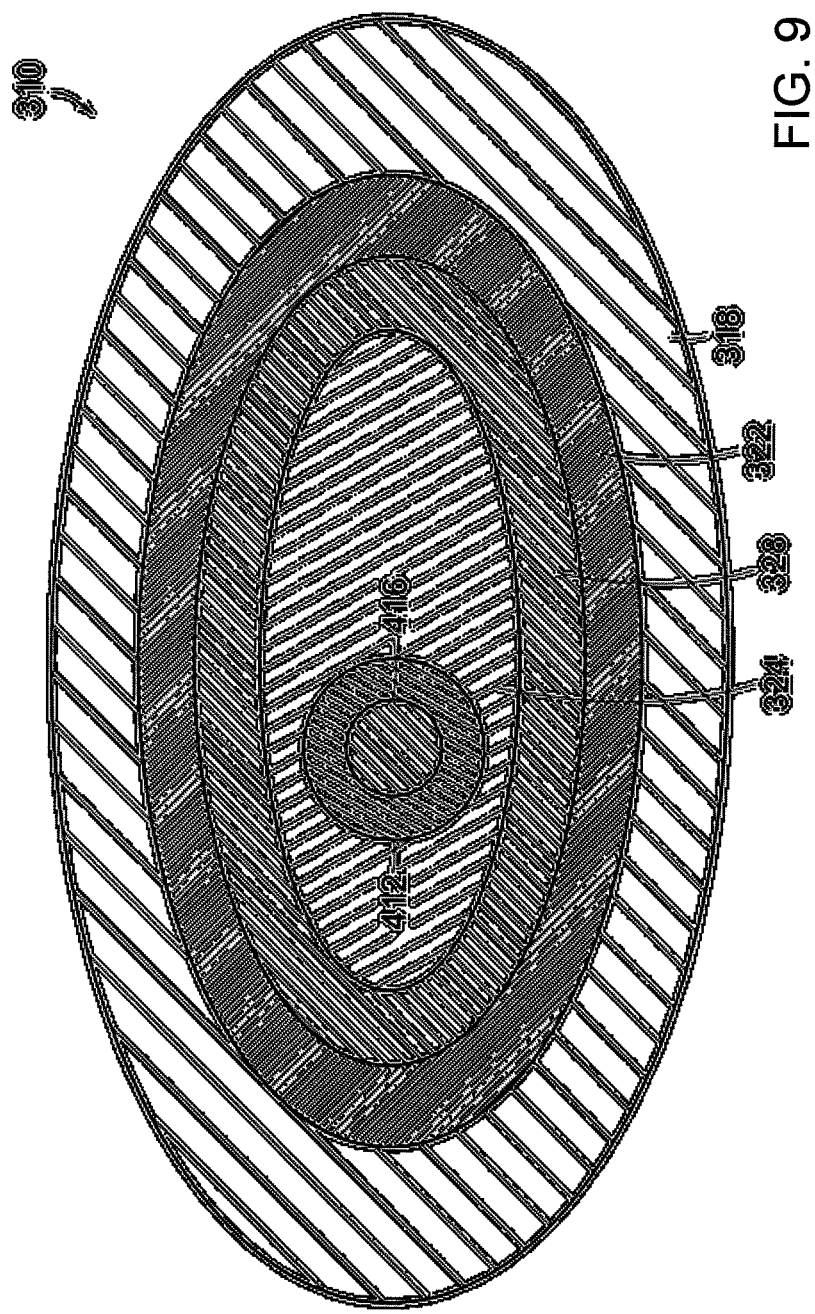
FIG. 9 illustrates a top view of the bone model corresponding to FIG. 8.

FIG. 9 illustrates a top view of the bone model 310 after the subtraction has taken place. The top view includes the identified area 416 from which the burr removed bone tissue penetrating into the boundary layer model 328. Because the depth of the burr model 314 penetrated into the boundary layer model 328 (as can be seen from FIG. 8) the processor draws the identified surface area 416 in the color white, the corresponding color of the boundary layer model 328. The top view also includes the identified area 412 from FIG. 7. The identified surface area 412 that remains visible, after surface area 416 is drawn in white, remains in the color green, the corresponding color of the implant layer model 324. This helps illustrate an example of the cumulative buffer approach. In the cumulative buffer approach, the starting point for FIG. 9 is FIG. 7, the previous update. From FIG. 7, the identified surface area for the penetration into the boundary layer model 328 was subtracted and drawn in the color corresponding to the boundary layer model 328 to generate the surface area 416. Cumulative subtraction can take place because there is no change in the viewing angle, which remains fixed. Thus the depths and surface areas can be subtracted from previous renderings. When drawing a three-dimensional image, the depth of the surface area 416 is greater than the depth of surface area 412, which is greater than the depth of the rest of the top surface of the implant layer model 324 because material has now been removed down to the boundary layer model 328.

Figure 10:
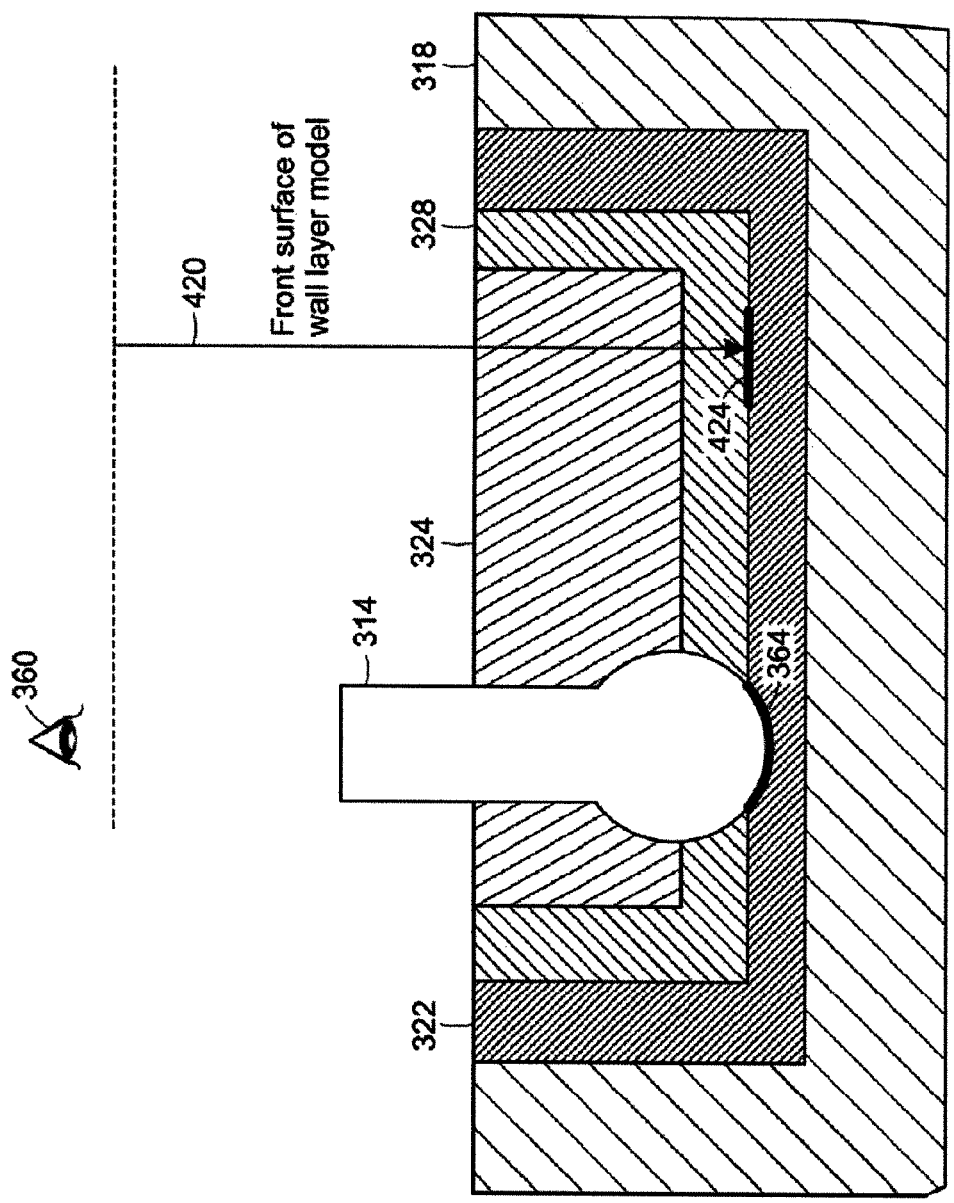
FIG. 10 illustrates the front view of the bone preparation model and the burr model using the same viewing angle illustrated in FIG. 8, with the burr model in a different position.

FIG. 10 illustrates the front view of the bone preparation model 310 and the burr model 314 using the same viewing angle illustrated in FIG. 8, represented by the eye 360. In FIG. 10, the position of the burr model 314 has changed from its position in FIG. 8 and has penetrated into the wall layer model 322. Similar to the process described above, the processor determines the depth (indicated by arrow 420) of front surfaces 424 of the top of the wall layer model 322. The processor will render depths of front surfaces 424 of the wall layer model 322 The processor identifies the surface area of the bone model 310 at the location of the burr model 314 where each pixel on a surface of the wall model layer 322 has depth less than the depths of the back surfaces 364 of the burr model 314, then draws the subtracted surface in the color red, the color corresponding to the wall layer model 322. This surface area represents the area from which bone material has been removed from the bone using the burr within the wall layer model 322. In some surgical computer systems, a haptic device can prevent a surgeon from moving the surgical instrument (represented by the burr model 314) past a boundary, such as a boundary represented by the wall layer model 322. For example, a surgical computer system can keep the burr model 314 (and thus the surgical instrument) from moving past the wall layer model 322 into the bone layer model 318 by using haptic guidance (e.g., force feedback), as described in above-referenced U.S. Patent Publication 2006/0142657.

Figure 11:
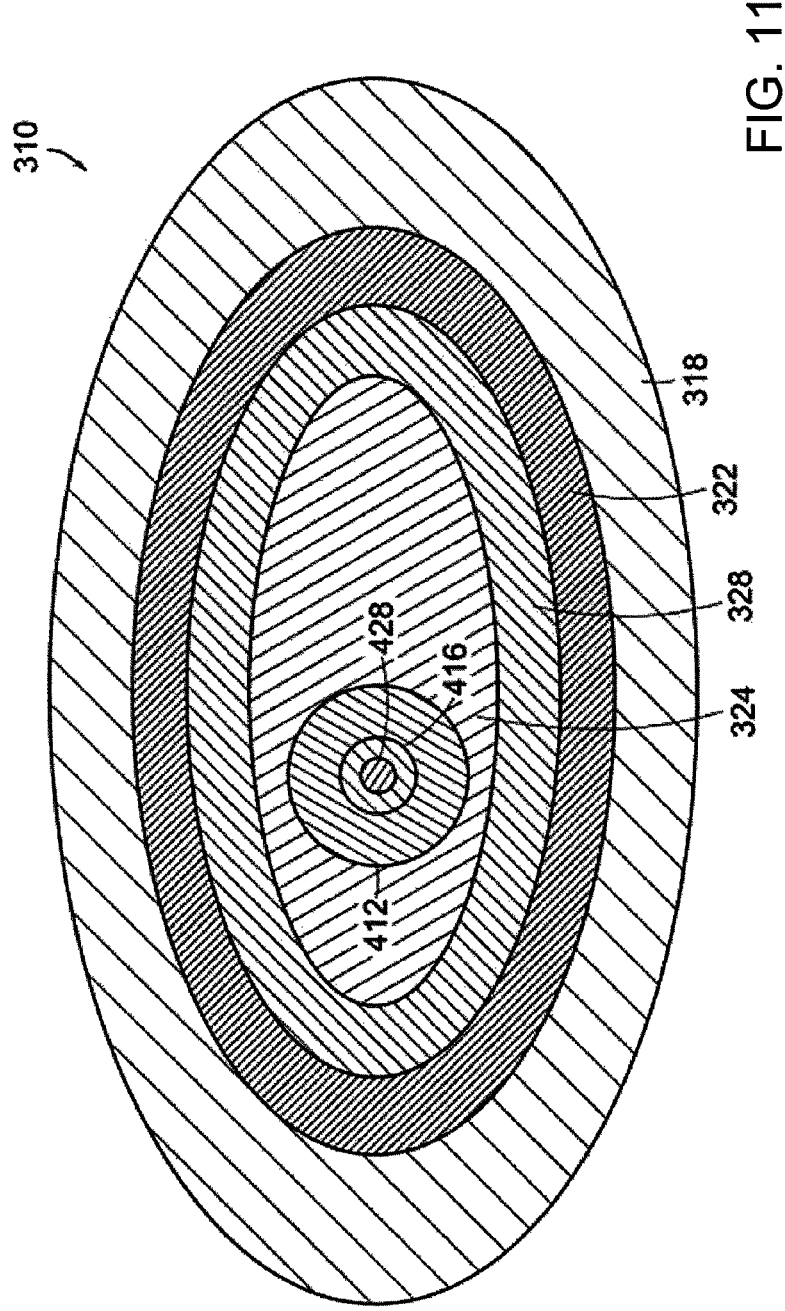
FIG. 11 illustrates a top view of the bone model corresponding to FIG. 10.

FIG. 11 illustrates a top view of the bone model 310 after the subtraction has taken place. The top view includes the identified area 428 from which the burr removed bone tissue penetrating into the wall layer model 322. Because the depth of the burr model 314 penetrated into the wall layer model 322 (as can be seen from FIG. 10) the processor draws the identified surface area 428 in the color red, the corresponding color of the wall layer model 322. The top view also includes the identified areas 412 and 416 from FIG. 9. The identified surface areas 412 and 416 that remain visible, after surface area 428 is drawn in red, remain in the color green and white, respectively, the colors representing the current layer penetration for that particular surface area. This again helps illustrate an example of the cumulative buffer approach. In the cumulative buffer approach, the starting point for FIG. 11 is FIG. 9, the previous update. From FIG. 9, the identified surface area for the penetration into the wall layer model 322 was subtracted and drawn in the color corresponding to the wall layer model 322 to generate the surface area 428. When drawing a three-dimensional image, the depth of the surface area 428 is greater than the depth of the surface area of 416, which is greater than the depth of the surface area 412, which is greater than the depth of the rest of the top surface of implant layer model 324 because material has now been removed down to the wall layer model 322.

Figure 12:
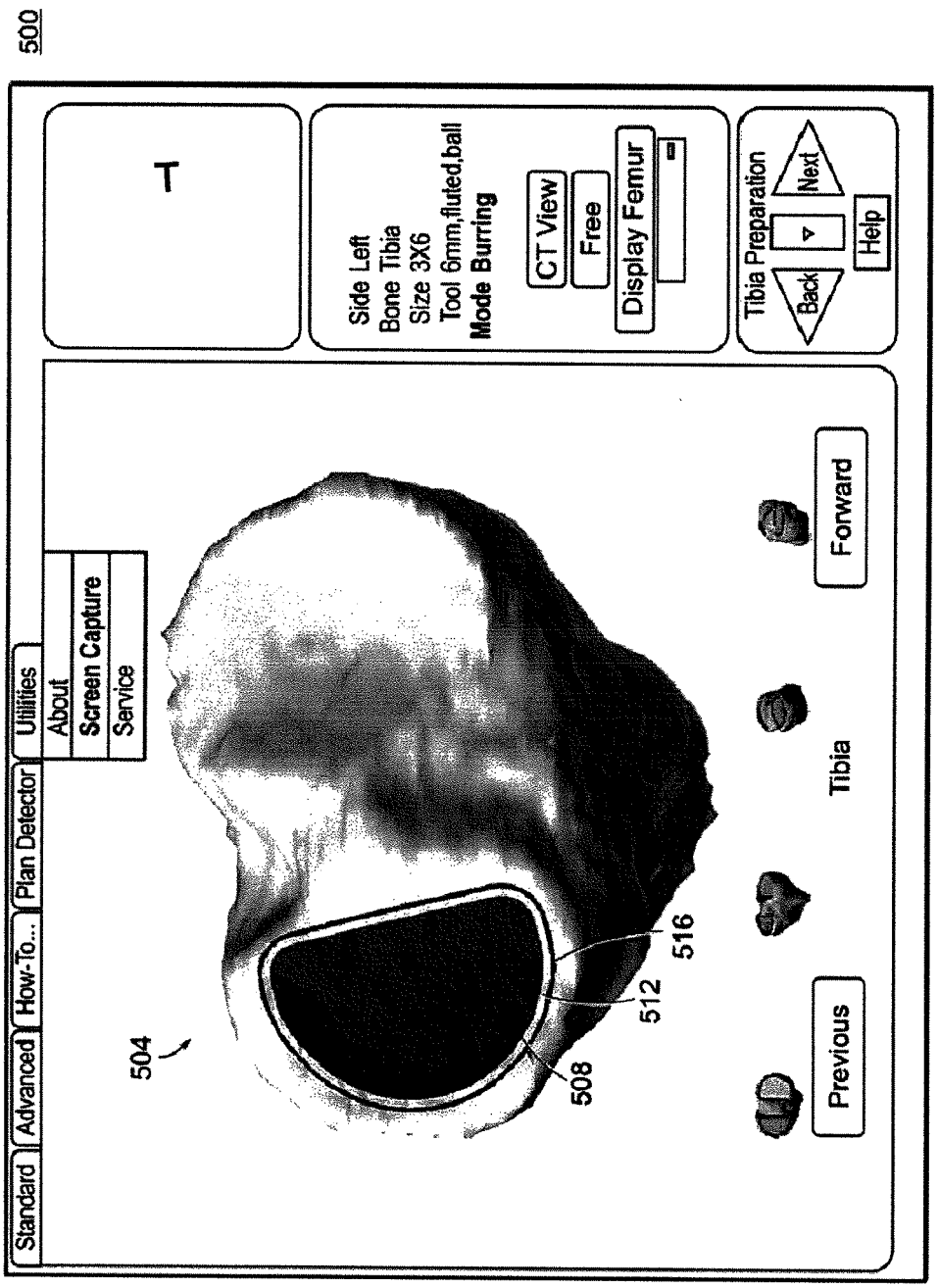
FIG. 12 illustrates an exemplary screen shot of a display of a tibia bone preparation visualization before tissue is removed.
Figure 13:
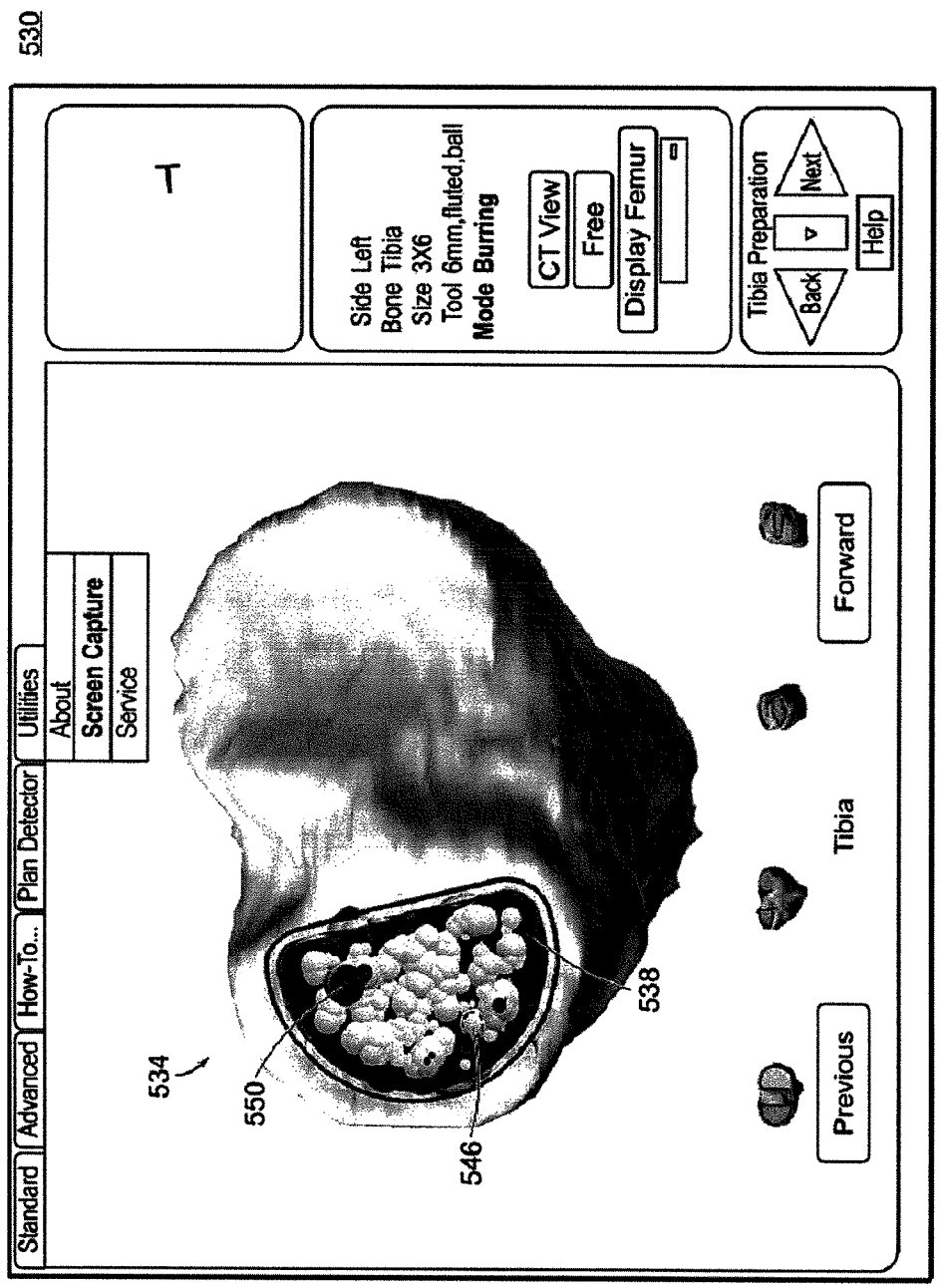
FIG. 13 illustrates an exemplary screen shot of a display of a tibia bone preparation visualization after tissue is removed.
Figure 14:
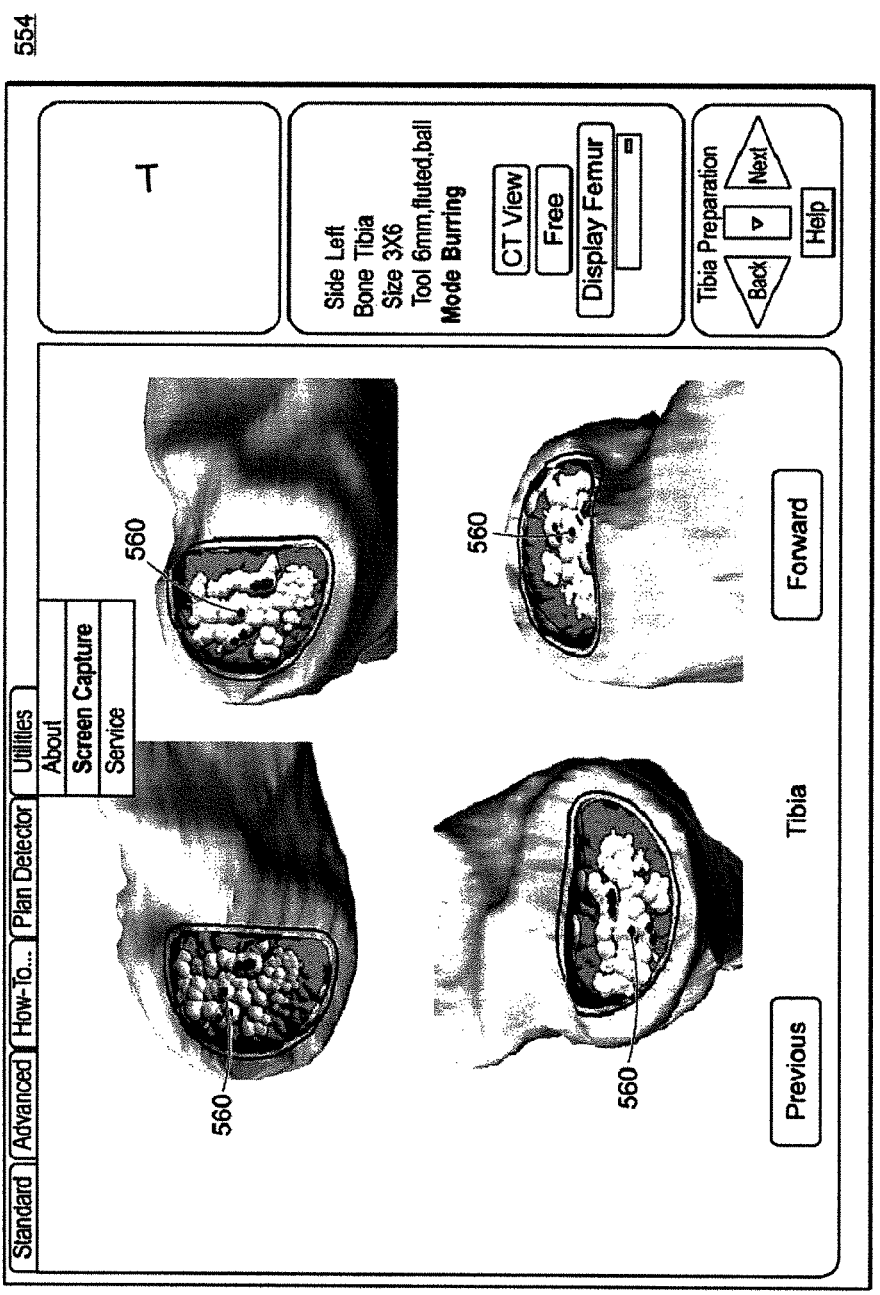
FIG. 14 illustrates an exemplary screen shot of a multiple displays at different viewing angles of a tibia bone preparation visualization after tissue is removed.

The techniques described herein can be applied to visualize bone cutting or preparation for a knee replacement procedure, such as a tibia bone preparation for inserting a tibial implant using a surgical computer system. FIGS. 12-14 illustrate exemplary screenshots of such visualizations. FIG. 12 illustrates a screen shot 500 displaying a view 504 representing a tibia bone model including a representation 508 of a tibial implant layer model (color green), a representation 512 of a boundary layer model (e.g., displayed using the color white), and a representation 516 of a wall layer model (e.g., displayed using the color red). This is the same exemplary layer modeling described above in connection with FIGS. 2-11. The area 508 represented in green indicates the area of tissue to be removed so that a planned tibial implant can be inserted into the tibia.

FIG. 13 illustrates a screen shot 530 displaying a view 534 of the tibia bone preparation after surgical cutting or burring has taken place. The view 534 illustrates how the layer depth techniques can be used in a bone preparation visualization. The colors represent the depth of the surgical burring at particular locations. For example, in area 538, the color of the surface area is green, indicating that the surgical burr did not penetrate into the boundary layer, but remained in the implant layer. This indicates to the surgeon that additional removal of tissue is necessary to be able to insert the implant into the tibia as planned. In area 546, the color of the surface area is white, indicating that the surgical burr did penetrate into the boundary layer. This indicates to the surgeon that additional removal of tissue is not necessary in this area, as the required depth was reached to be able to insert the implant into the tibia as planned. In area 550, the color of the surface area is red, indicating that the surgical burr did penetrate past the boundary layer and into the wall layer. This indicates to the surgeon that depth of burr penetration was too deep. In some surgical computer systems, a haptic device can prevent a surgeon from moving the surgical instrument past the boundary represented by the wall layer model by using haptic guidance, as described above. In such systems, the red area 550 also indicates where the haptic device stopped the surgeon from cutting any further into the bone.

The visualization shown in the screen shot 530 is generated using the cumulative buffering algorithm described herein using a CSG technique. For example, the visualization of a burring process starts from FIG. 12. When the burring process starts, a CSG subtraction is performed (e.g., primitives for applicable models added as leafs to a CSG tree using appropriate Boolean operators) to remove burring tissue from bone model, and the subtracted image is buffered for the next subtraction. When the surgeon begins the burring process again (e.g., moves the burr), the display can start at its current state. As the burr is moved and tissue is removed, the subtraction is repeated on the then current display to cumulatively generate an updated display. For example, as the burr is penetrated into the area 538, the process calculates the depths until the burr penetrates the boundary layer. At that time, the location of the burr within the area 538 would cause a change in the display from green to white. Once that color change was made, it would stay in the cumulative buffer and any change in the burr location would then be subtracted from that display.

One reason the display can be generated using a cumulative technique is because the viewing angle remains fixed. If the viewing angle were to change, the display would have to be regenerated using all of the previous burr locations, from the start, to regenerate the display at the new viewing angle. For example, if the sampling rate for the position of the burr is 10 Hz, after a 5 minute burring process, the number of burr primitives would be 300. To redisplay the new viewing angle, all 300 primitives would have to be subtracted again at the new viewing angle. FIG. 14 illustrates a screen shot 554 in which multiple viewing angles are displayed at the same time. This advantageously lessens the risk that a new viewing angle would need to be displayed. Because each viewing angle uses the cumulative buffering, all four of the displays can be updated with each burr sample to simultaneously maintain the four views. An area 560 indicates a depth that has penetrated the wall layer and is displayed in red. This area 560 is referenced so that the reader can orient herself with the same spot in each of the four different viewing angles.

Figure 15:
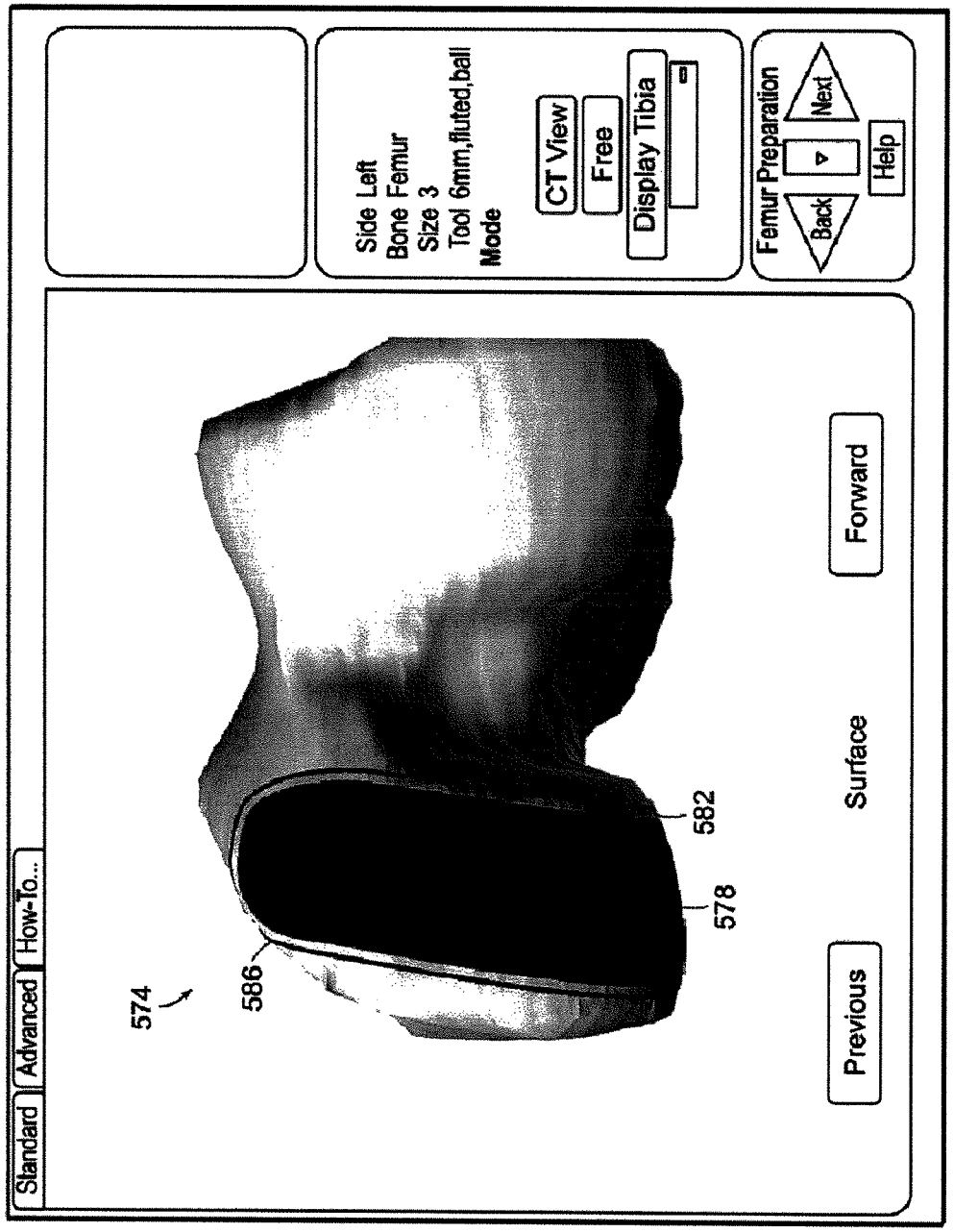
FIG. 15 illustrates an exemplary screen shot of a display of a femur bone preparation visualization before tissue is removed.
Figure 16:
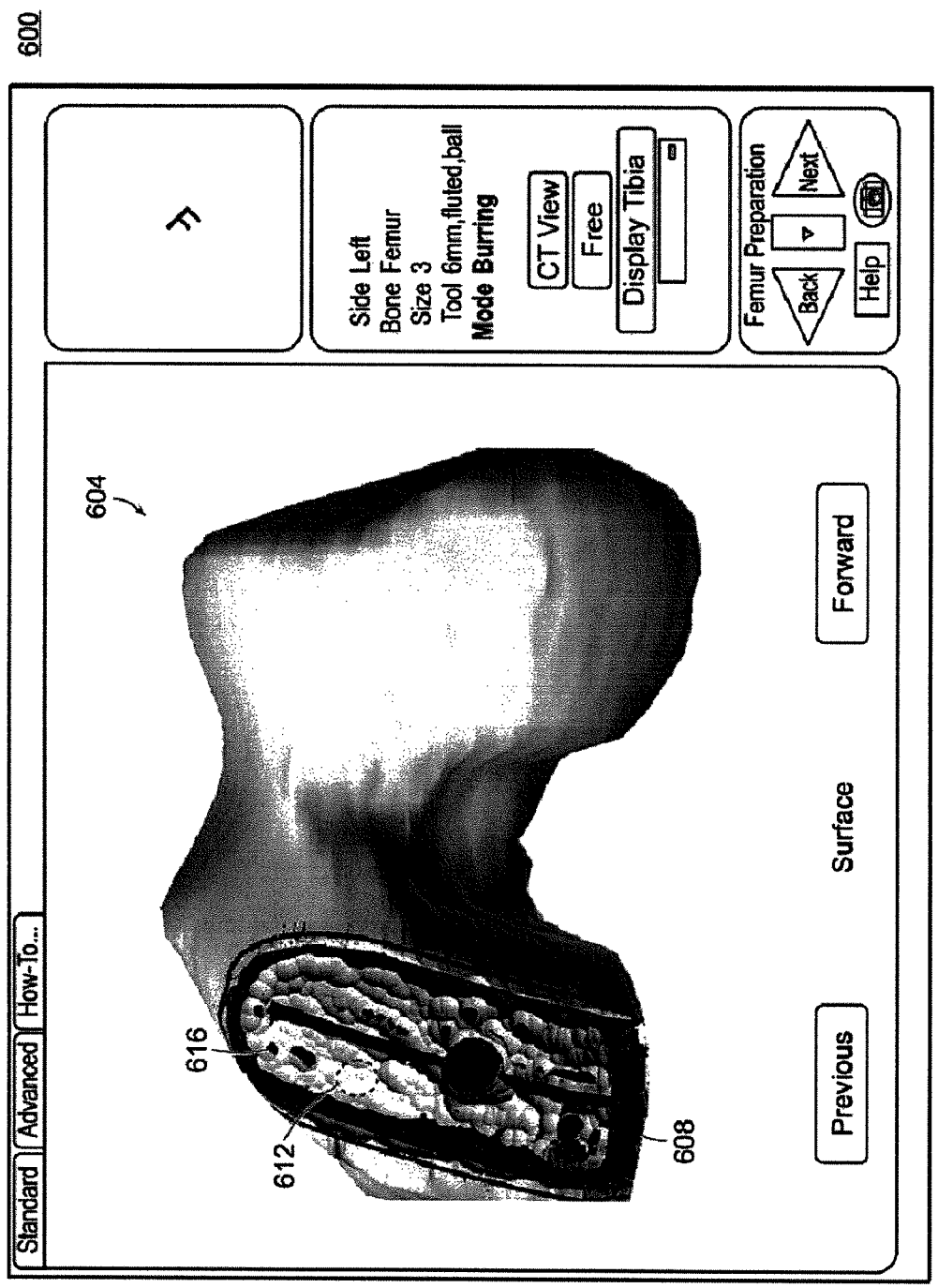
FIG. 16 illustrates an exemplary screen shot of a display of a femur bone preparation visualization after tissue is removed.

Similarly, the techniques described herein can be applied to visualize a femur bone preparation for implanting a femoral implant using a surgical computer system. FIGS. 15-16 illustrate exemplary screenshots of such visualizations. FIG. 15 illustrates a screen shot 570 displaying a view 574 representing a femur bone model including a representation 578 of a femoral implant layer model (color green), a representation 582 of a boundary layer model (e.g., displayed using the color white), and a representation 586 of a wall layer model (e.g., displayed using the color red). This is the same exemplary layer modeling described above in connection with FIGS. 2-11. The area 578 represented in green indicates the area of tissue to be removed so that a planned femoral implant can be inserted into the femur.

FIG. 16 illustrates a screen shot 600 displaying a view 604 of the femur bone preparation after surgical burring has taken place. The view 604 illustrates how the layer depth techniques can be used in a bone preparation visualization. The colors represent the depth of the surgical burring at particular locations. For example, in area 608, the color of the surface area is green, indicating that the surgical burr did not penetrate into the boundary layer, but remained in the implant layer. This indicates to the surgeon that additional removal of tissue is necessary to be able to insert the implant into the femur as planned. In area 612, the color of the surface area is white, indicating that the surgical burr did penetrate into the boundary layer. This indicates to the surgeon that additional removal of tissue is not necessary in this area, as the required depth was reached to be able to insert the implant into the femur as planned. In area 616, the color of the surface area is red, indicating that the surgical burr did penetrate past the boundary layer and into the wall layer. This indicates to the surgeon that depth of burr penetration was too deep. In some surgical computer systems, a haptic device can prevent a surgeon from moving the surgical instrument past the boundary represented by the wall layer model by using haptic guidance, as described above. In such systems, the red area 616 also indicates where the haptic device stopped the surgeon from cutting any further into the bone.

The visualization shown in the screen shot 600 is generating using the cumulative buffering algorithm described herein using a CSG technique. When the surgeon begins the burring process again, the display can start at its current state. As the burr is moved and tissue is removed, the subtraction is performed on the current display to cumulatively generate an updated display. For example, as the burr is penetrated into the area 608, the process calculates the depths until the burr penetrates the boundary layer. At that time, the location of the burr within the area 608 would cause a change in the display from green to white. Once that color change was made, it would stay in the cumulative buffer and any change in the burr location would then be subtracted from that display.

The following is an exemplary pseudo-code description of CSG bone preparation rendering cycle:

```
CopyColorBuffer( );
TrimWithPrimitive (back_surface_burr, glDepthFunc=GREATER);
DrawCSGPrimitive (back_surface_burr, RED);
TrimWithPrimitive (front_surface_implant, glDepthFunc=LESS);
DrawCSGPrimitive (back_surface_burr, GREEN);
TrimWithPrimitive (front_surface_white_layer, glDepthFunc=LESS);
DrawCSGPrimitive (back_surface_burr, WHITE);
TrimWithPrimitive (front_surface_red_layer, glDepthFunc=LESS);
DrawCSGPrimitive (back_surface_burr, RED);
SaveColorBuffer( );
DrawCSGPrimitive (front_surface_burr, BLUE);
```

The CopyColorBuffer( ) method copies the saved image to the image buffer. The SaveColorBuffer method copies the image buffer to another buffer in video card memory or in main memory. The TrimWithPrimitive method specifies the area that satisfies the condition. For example, TrimWithPrimitive (back_surface_burr, glDepthFunc=GREATER) finds the area where each pixel has depth (distance from the view point) less than the depth of the pixel on the back surface (the surface facing away from the viewer) of the burr. The method DrawCSGPrimitive (back_surface_burr, RED) draws the back surface of the burr with the indicated color in the area found by TrimWithPrimitive.

In operation, a processor executing the code copies the saved image from the previous update to the image buffer. The processor renders the depth of the back surface of burr in the depth buffer, and trims the surface if the burr depth is less than the current depth. Trimming the surface in this context means finding the surface area that satisfies the condition of the "glDepthFunc" that is included in the passed parameters of the method. The processor draws the trimmed back surface of the burr in red (in the image buffer) and updates the depth buffer at the burr location. In this embodiment, the red color is used first because it will most likely be overwritten by the other colors as the burr penetrates the bone inside of the wall layer model 322. However, if the burr is outside of the wall layer model 322, for example as shown in area 386 in FIG. 5, this technique will keep the area 386 red and that area will not be overwritten by the other colors during subsequent processing, indicating that the burr is outside of a set boundary.

The processor renders the depth of the front surface of the green model and trims the surface if the depth is greater than the current depth. Trimming the surface in this context means finding the surface area that satisfies the condition of the "glDepthFunc" that is included in the passed parameters of the method. The processor draws the back surface of the burr in the trimmed area in green in the image buffer. The processor renders the depth of the front surface of the white model and trims the surface if the depth is greater than the current depth. The processor draws the back surface of the burr in the trimmed area in white. The processor renders the depth of the front surface of the red model and trims the surface if the depth is greater than the current depth. The processor draws the back surface of the burr in the trimmed area in red. The processor saves the current rendered image. The processor displays the front surface of the burr in its new position and angle.

Although the pseudo code and description use the same exemplary layering models and colors as the descriptions above, this is not a limitation. In the general case, any number of models can be ordered from top to bottom. In the exemplary embodiment the bottom model is treated differently since it is not "subtracted".

Figure 17:
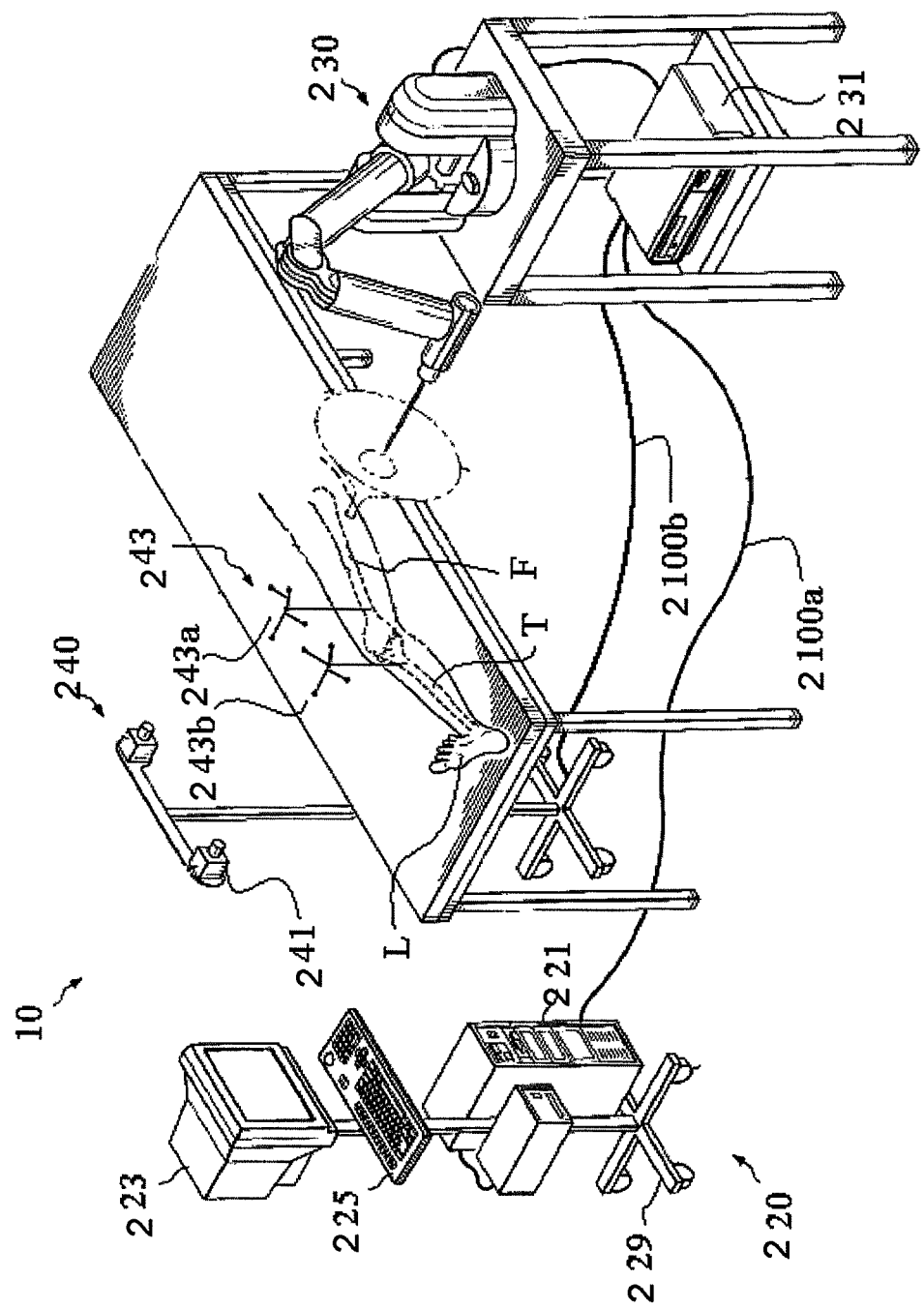
FIG. 17 illustrates an exemplary surgical computer system for cumulative buffering for surface imaging.

FIG. 17 shows an embodiment of an exemplary surgical computer system 210 in which the techniques described above can be implemented. The surgical system 210 includes a computing system 220, a haptic device 230, and a tracking (or localizing) system 240. In operation, the surgical system 210 enables comprehensive, intraoperative surgical planning. The surgical system 210 also provides haptic guidance to a user (e.g., a surgeon) and/or limits the user's manipulation of the haptic device 230 as the user performs a surgical procedure. Although included for completeness in the illustrated embodiment, the haptic device 230 and its associated hardware and software is not necessary to perform the techniques described herein.

The computing system 220 includes a computer 221, a display device 223, and an input device 225. The computing system 220 may also include a cart 229. The computing system 220 includes hardware and software for operation and control of the surgical system 210. Such hardware and/or software is configured to enable the system 210 to perform the techniques described herein. For example, the computer 221 and/or the display device 223 can include one or more video cards with one or more graphics processing units (GPUs) that have been configured to enable the system 210 to perform the techniques described herein.

The computer 221 may be any known computing system but is preferably a programmable, processor-based system. For example, the computer 221 may include a microprocessor, a hard drive, random access memory (RAM), read only memory (ROM), input/output (I/O) circuitry, and any other well-known computer component. The computer 221 is preferably adapted for use with various types of storage devices (persistent and removable), such as, for example, a portable drive, magnetic storage (e.g., a floppy disk), solid state storage (e.g., a flash memory card), optical storage (e.g., a compact disc or CD), and/or network/Internet storage. The computer 221 may comprise one or more computers, including, for example, a personal computer (e.g., an IBM-PC compatible computer) or a workstation (e.g., a SUN or Silicon Graphics workstation) operating under a Windows, MS-DOS, UNIX, or other suitable operating system and preferably includes a graphical user interface (GUI).

The display device 223 is a visual interface between the computing system 220 and the user. The display device 223 is connected to the computer 221 and may be any device suitable for displaying text, images, graphics, and/or other visual output. For example, the display device 223 may include a standard display screen (e.g., LCD, CRT, plasma, etc.), a touch screen, a wearable display (e.g., eyewear such as glasses or goggles), a projection display, a head-mounted display, a holographic display, and/or any other visual output device. The display device 223 may be disposed on or near the computer 221 (e.g., on the cart 229 as shown in FIG. 17) or may be remote from the computer 221 (e.g., mounted on a wall of an operating room or other location suitable for viewing by the user). The display device 223 is preferably adjustable so that the user can position/reposition the display device 223 as needed during a surgical procedure. For example, the display device 223 may be disposed on an adjustable arm (not shown) that is connected to the cart 229 or to any other location well-suited for ease of viewing by the user. The display device 223 may be used to display any information useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy, tools, implants, etc.), digital or video images, registration information, calibration information, patient data, user data, measurement data, software menus, selection buttons, status information, and the like.

In addition to the display device 223, the computing system 220 may include an acoustic device (not shown) for providing audible feedback to the user. The acoustic device is connected to the computer 221 and may be any known device for producing sound. For example, the acoustic device may comprise speakers and a sound card, a motherboard with integrated audio support, and/or an external sound controller. In operation, the acoustic device may be adapted to convey information to the user. For example, the computer 221 may be programmed to signal the acoustic device to produce a sound, such as a voice synthesized verbal indication "DONE," to indicate that a step of a surgical procedure is complete. Similarly, the acoustic device may be used to alert the user to a sensitive condition, such as producing a beep to indicate that a surgical cutting tool is nearing a critical portion of soft tissue.

The input device 225 of the computing system 220 enables the user to communicate with the surgical system 210. The input device 225 is connected to the computer 221 and may include any device enabling a user to provide input to a computer. For example, the input device 225 can be a known input device, such as a keyboard, a mouse, a trackball, a touch screen, a touch pad, voice recognition hardware, dials, switches, buttons, a trackable probe, a foot pedal, a remote control device, a scanner, a camera, a microphone, and/or a joystick.

The computing system 220 is coupled to the computing device 231 via an interface 2100a and to a detection device 241 via an interface 2100b. The interfaces 2100a and 2100b can include a physical interface and a software interface. The physical interface may be any known interface such as, for example, a wired interface (e.g., serial, USB, Ethernet, CAN bus, and/or other cable communication interface) and/or a wireless interface (e.g., wireless Ethernet, wireless serial, infrared, and/or other wireless communication system). The software interface may be resident on the computer 221 and/or the computer 231. In some embodiments, computer 221 and 231 are the same computing device.

The system 210 also includes a tracking (or localizing) system 240 that is configured to determine a pose (i.e., position and orientation) of one or more objects during a surgical procedure to detect movement of the object(s). For example, the tracking system 240 may include a detection device that obtains a pose of an object with respect to a coordinate frame of reference of the detection device. As the object moves in the coordinate frame of reference, the detection device tracks the pose of the object to detect (or enable the surgical system 210 to determine) movement of the object. As a result, the computing system 220 can capture data in response to movement of the tracked object or objects. Tracked objects may include, for example, tools/instruments, patient anatomy, implants/prosthetic devices, and components of the surgical system 210. Using pose data from the tracking system 240, the surgical system 210 is also able to register (or map or associate) coordinates in one space to those in another to achieve spatial alignment or correspondence (e.g., using a coordinate transformation process as is well known). Objects in physical space may be registered to any suitable coordinate system, such as a coordinate system being used by a process running on the computer 221 and/or the computer 231. For example, utilizing pose data from the tracking system 240, the surgical system 210 is able to associate the physical anatomy with a representation of the anatomy (such as an image displayed on the display device 223). Based on tracked object and registration data, the surgical system 210 may determine, for example, a spatial relationship between the image of the anatomy and the relevant anatomy.

Registration may include any known registration technique, such as, for example, image-to-image registration (e.g., monomodal registration where images of the same type or modality, such as fluoroscopic images or MR images, are registered and/or multimodal registration where images of different types or modalities, such as MRI and CT, are registered); image-to-physical space registration (e.g., image-to-patient registration where a digital data set of a patient's anatomy obtained by conventional imaging techniques is registered with the patient's actual anatomy); and/or combined image-to-image and image-to-physical-space registration (e.g., registration of preoperative CT and MRI images to an intraoperative scene). The computer system 210 may also include a coordinate transform process for mapping (or transforming) coordinates in one space to those in another to achieve spatial alignment or correspondence. For example, the surgical system 210 may use the coordinate transform process to map positions of tracked objects (e.g., patient anatomy, etc.) into a coordinate system used by a process running on the computer 231 and/or the computer 221. As is well known, the coordinate transform process may include any suitable transformation technique, such as, for example, rigid-body transformation, non-rigid transformation, affine transformation, and the like.

The tracking system 240 may be any tracking system that enables the surgical system 210 to continually determine (or track) a pose of the relevant anatomy of the patient. For example, the tracking system 240 may comprise a non-mechanical tracking system, a mechanical tracking system, or any combination of non-mechanical and mechanical tracking systems suitable for use in a surgical environment. The non-mechanical tracking system may include an optical (or visual), magnetic, radio, or acoustic tracking system. Such systems typically include a detection device adapted to locate in predefined coordinate space specially recognizable trackable elements (or trackers) that are detectable by the detection device and that are either configured to be attached to the object to be tracked or are an inherent part of the object to be tracked. For example, a trackable element may include an array of markers having a unique geometric arrangement and a known geometric relationship to the tracked object when the trackable element is attached to the tracked object. The known geometric relationship may be, for example, a predefined geometric relationship between the trackable element and an endpoint and axis of the tracked object. Thus, the detection device can recognize a particular tracked object, at least in part, from the geometry of the markers (if unique), an orientation of the axis, and a location of the endpoint within a frame of reference deduced from positions of the markers. The markers may include any known marker, such as, for example, extrinsic markers (or fiducials) and/or intrinsic features of the tracked object. Extrinsic markers are artificial objects that are attached to the patient (e.g., markers affixed to skin, markers implanted in bone, stereotactic frames, etc.) and are designed to be visible to and accurately detectable by the detection device. Intrinsic features are salient and accurately locatable portions of the tracked object that are sufficiently defined and identifiable to function as recognizable markers (e.g., landmarks, outlines of anatomical structure, shapes, colors, or any other sufficiently recognizable visual indicator). The markers may be located using any suitable detection method, such as, for example, optical, electromagnetic, radio, or acoustic methods as are well known. For example, an optical tracking system having a stationary stereo camera pair sensitive to infrared radiation may be used to track markers that emit infrared radiation either actively (such as a light emitting diode or LED) or passively (such as a spherical marker with a surface that reflects infrared radiation). Similarly, a magnetic tracking system may include a stationary field generator that emits a spatially varying magnetic field sensed by small coils integrated into the tracked object.

In one embodiment, as shown in FIG. 17, the tracking system 240 includes a non-mechanical tracking system. In this embodiment, the non-mechanical tracking system is an optical tracking system that comprises a detection device 241 and at least one trackable element (or tracker) configured to be disposed on (or incorporated into) a tracked object and detected by the detection device 241. In FIG. 17, the detection device 41 includes, for example, a stereo camera pair sensitive to infrared radiation and positionable in an operating room where the surgical procedure will be performed. The tracker is configured to be affixed to the tracked object in a secure and stable manner and includes an array of markers having a known geometric relationship to the tracked object. The markers may be active (e.g., light emitting diodes or LEDs) or passive (e.g., reflective spheres, a checkerboard pattern, etc.) and preferably have a unique geometry (e.g., a unique geometric arrangement of the markers) or, in the case of active, wired markers, a unique firing pattern. In operation, the detection device 241 detects positions of the markers, and the unique geometry (or firing pattern) and known geometric relationship to the tracked object enable the surgical system 210 to calculate a pose of the tracked object based on the positions of the markers.

The non-mechanical tracking system may include a trackable element (or tracker) for each object the user desires to track. For example, in one embodiment, the non-mechanical tracking system includes anatomy trackers 243a and 243b, generally 243 (to track patient anatomy).

In FIG. 17, the anatomy tracker 243 is disposed on a relevant portion of a patient's anatomy (such as a bone) and is adapted to enable the relevant anatomy to be tracked by the detection device 241. The anatomy tracker 243 includes a fixation device for attachment to the anatomy. The fixation device may be, for example, a bone pin, surgical staple, screw, clamp, wearable device, intramedullary rod, or the like. In one embodiment, the anatomy tracker 243 is configured for use during knee replacement surgery to track a femur F and a tibia T of a patient. In this embodiment, as shown in FIG. 17, the anatomy tracker 243 includes a first tracker 243a adapted to be disposed on the femur F and a second tracker 243b adapted to be disposed on the tibia T.

Presently preferred embodiments are illustrated in the drawings. Although this specification refers primarily to a knee joint, it should be understood that the subject matter described herein is applicable to other joints in the body, such as, for example, a shoulder, elbow, wrist, spine, hip, or ankle and to any other orthopedic and/or musculoskeletal implant, including implants of conventional materials and more exotic implants, such as orthobiologics, drug delivery implants, and cell delivery implants.

The above-described techniques can be implemented in digital electronic circuitry, or in computer hardware, firmware, software, or in combinations of them. The implementation can be as a computer program product, i.e., a computer program tangibly embodied in an information carrier, e.g., in a machine-readable storage device, for execution by, or to control the operation of, data processing apparatus, e.g., a programmable processor, a computer, or multiple computers. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps can be performed by one or more programmable processors executing a computer program to perform functions of the invention by operating on input data and generating output. Method steps can also be performed by, and apparatus can be implemented as, special purpose logic circuitry, e.g., an FPGA (field programmable gate array) or an ASIC (application-specific integrated circuit). Modules can refer to portions of the computer program and/or the processor/special circuitry that implements that functionality.

The above described techniques can be implemented in a distributed computing system that includes a back-end component, e.g., as a data server, and/or a middleware component, e.g., an application server, and/or a front-end component, e.g., a client computer having a graphical user interface and/or a Web browser through which a user can interact with an example implementation, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet, and include both wired and wireless networks.

The computing system can include clients and servers. A client and server are generally remote from each other and typically interact through a communication network. The relationship of client and server arises by virtue of computer programs running on the respective computers and having a client-server relationship to each other.

Comprise, include, have and/or plural forms of each are open ended and include the listed parts and can include additional parts that are not listed. And/or is also open ended and includes one or more of the listed parts and combinations of the listed parts.

The invention has been described in terms of particular embodiments. The alternatives described herein are examples for illustration only and not to limit the alternatives in any way. The steps of the invention can be performed in a different order and still achieve desirable results. Other embodiments are within the scope of the following claims.

What is claimed is:
1. A method of cumulative buffering for surface imaging, the method comprising:

representing a workpiece model using a plurality of layer models;
displaying a display image of the workpiece model based on a previous update, the previous update comprising a previous display image and one or more previous subtractions made to the previous display image;
buffering a display image saved from the previous update;
subtracting a model representing a tool from the buffered display image to generate a subtracted display image comprising the one or more previous subtractions and a new subtraction, the new subtraction representing a top surface area of a portion of the buffered display image that is subtracted;
displaying the subtracted display image at a fixed angle on the display by subtracting the new subtraction from the buffered display image and drawing a representation of a surface area of the buffered display image located underneath the top surface area without clearing the buffered display image from the display;
wherein the subtracted display image comprises a first image portion representing a subtraction made to an upper layer of the plurality of layer models and further comprising a second image portion representing a subtraction made to a lower layer of the plurality of layer models;
wherein the first image portion has at least one visual characteristic that is different from a visual characteristic of the second image portion; and
saving the subtracted display image as the previous update such that any subsequent subtractions are performed on the subtracted display image.

2. A method of claim 1, comprising displaying the model representing the tool using a CSG technique at the fixed angle.

3. A method of claim 1, comprising repeating the steps of buffering, subtracting, displaying, and saving in response to a received update of location of the tool.

4. A method of claim 1, wherein subtracting comprises:
determining depths of back surfaces of the model representing the tool; and
determining a surface area within the workpiece model at a location of the model representing the tool where each pixel on the surface has depth less than the depths of the back surfaces of the model representing the tool, and
wherein displaying comprises:
displaying the subtracted surface in the identified area in a corresponding color of a first layer model.

5. A method of claim 4, wherein the first layer model has a depth greater than a second layer model from the plurality of layer models at the location of the model representing the tool.

6. A method of claim 4, wherein determining further comprises determining each pixel on the surface area that has depth falling within a range of a depth of a front surface of the first layer model and a depth of a back surface of the first layer model, inclusive.

7. A method of claim 1, wherein subtracting comprises:
representing a workpiece model using a plurality of layer models, the plurality including a top most layer model, a bottom most layer model, and one or more intermediate layer models;
determining depths of front surfaces of the top most layer model;
identifying a surface area of the workpiece model where each pixel on the surface area has depth greater than the depths of front surfaces of the top most layer model; and
displaying the identified surface area in a corresponding color of the top most layer model.

8. A method of claim 7, wherein subtracting comprises:
for each of the one or more intermediate layer models,
determining depths of front surfaces of a particular intermediate layer model;
identifying a surface area of the workpiece model where each pixel on the surface area has depth greater than the depths of front surfaces of the particular intermediate layer model; and
displaying the identified surface area in a corresponding color of the particular intermediate layer model.

9. A method of claim 8, wherein subtracting comprises:
determining depths of front surfaces of the bottom most layer model;
identifying a surface area of the workpiece model where each pixel on the surface area has depth greater than the depths of front surfaces of the bottom most layer model; and
displaying the identified surface area in a corresponding color of the bottom most layer model.

10. A method of claim 1, wherein subtracting comprises:
determining depths of back surfaces of the model representing the tool;
identifying a surface area of a workpiece model at a location of the model representing the tool where each pixel on the surface area has depth less than the depths of the back surfaces of the model representing the tool;
displaying the identified surface area in a corresponding color of a wall layer model if the location of the model representing the tool is outside a boundary of the wall layer model; and
displaying the identified surface area in a color corresponding to an appropriate layer model based on depth if the location of the model representing the tool is within the boundary of the wall layer model.

11. A method of claim 1, wherein the display image is a first display image and the fixed angle is a first fixed angle, the method comprising:
buffering a second display image saved from a previous update, the second display image having a viewing angle at a second fixed angle different than the first fixed angle;
subtracting the model representing the tool from the buffered second display image using the CSG technique;
displaying the subtracted second display image at the second fixed angle; and
saving the subtracted second display image.

12. A method of claim 1, comprising representing an implant within the display image.

13. A method of claim 1, comprising representing an implant within the display image using a first layer model from a plurality of layer models.

14. A method of claim 1, wherein buffering comprises copying the display image saved from the previous update.

15. A method of claim 1, wherein the display image is based on a medical image associated with a patient.

16. A method of claim 1, wherein the model representing the tool comprises a burr model.

17. A method of claim 16, wherein the burr model comprises a spherical primitive.

18. A computer program product, tangibly embodied in a non-transitory computer readable medium, the computer program product including instructions being operable to cause a data processing apparatus to:
represent a workpiece model using a plurality of layer models;

display a display image of the workpiece model based on a previous update, the previous update comprising a previous display image and one or more previous subtractions made to the previous display image;

buffer a display image saved from the previous update;

subtract a model representing a tool from the buffered display image using a CSG technique to generate a subtracted display image comprising the one or more previous subtractions and a new subtraction, the new subtraction representing a top surface area of a portion of the buffered display image that is subtracted;

display the subtracted display image at a fixed angle on the display by subtracting the new subtraction from the buffered display image and drawing a representation of a surface area of the buffered display image located underneath the top surface without clearing the buffered display image from the display;

wherein the subtracted display image comprises a first image portion representing a subtraction made to an upper layer of the plurality of layer models and further comprising a second image portion representing a subtraction made to a lower layer of the plurality of layer models;

wherein the first image portion has at least one visual characteristic that is different from a visual characteristic of the second image portion; and save the subtracted display image as the previous update such that any subsequent subtractions are performed on the subtracted display image.

19. A surgical computer system comprising:

at least one video card configured to:

represent a workpiece model using a plurality of layer models;

display a display image of the workpiece model based on a previous update, the previous update comprising a previous display image and one or more previous subtractions made to the previous display image;

buffer a display image saved from the previous update;

subtract a model representing a tool from the buffered display image using a CSG technique to generate a subtracted display image comprising the one or more previous subtractions and a new subtraction, the new subtraction representing a top surface area of a portion of the buffered display image that is subtracted;

display the subtracted display image at a fixed angle on the display by subtracting the new subtraction from buffered display image and drawing a representation of a surface area of the buffered display image located underneath the top surface without clearing the buffered display image from the display;

wherein the subtracted display image comprises a first image portion representing a subtraction made to an upper layer of the plurality of layer models and further comprising a second image portion representing a subtraction made to a lower layer of the plurality of layer models;

wherein the first image portion has at least one visual characteristic that is different from a visual characteristic of the second image portion; and save the subtracted display image as the previous update such that any subsequent subtractions are performed on the subtracted display image.

\* \* \* \* \*